(12) United States Patent
Wimalasena

(10) Patent No.: US 12,042,364 B2
(45) Date of Patent: *Jul. 23, 2024

(54) DARK-TINTED NONWOVEN WEBS

(71) Applicant: The Procter & Gamble Company, Cincinnati, OH (US)

(72) Inventor: Nirosha Seth Wimalasena, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 575 days.

This patent is subject to a terminal disclaimer.

(21) Appl. No.: 16/889,850

(22) Filed: Jun. 2, 2020

(65) Prior Publication Data
US 2020/0375813 A1  Dec. 3, 2020

Related U.S. Application Data

(60) Provisional application No. 62/856,454, filed on Jun. 3, 2019.

(51) Int. Cl.
*A61F 13/49* (2006.01)
*A61F 13/15* (2006.01)
*D04H 1/42* (2012.01)

(52) U.S. Cl.
CPC ........ *A61F 13/49* (2013.01); *A61F 13/15203* (2013.01); *D04H 1/42* (2013.01); *A61F 2013/15243* (2013.01); *A61F 2013/15406* (2013.01); *A61F 2013/49092* (2013.01)

(58) Field of Classification Search
CPC .............. A61F 13/49; A61F 13/15203; A61F 2013/15243; A61F 2013/15406; A61F 2013/49092; A61F 13/494; A61F 13/51478; A61F 13/475; D04H 1/42; D04H 1/4374; D04H 3/005; D04H 3/016
See application file for complete search history.

(56) References Cited

U.S. PATENT DOCUMENTS 4,340,563 A   7/1982  Appel et al.
5,571,604 A   11/1996 Sprang et al.
(Continued)

FOREIGN PATENT DOCUMENTS

CN   1369027 A   9/2002
CN   1443053 A   9/2003
(Continued)

OTHER PUBLICATIONS

All Office Actions; U.S. Appl. No. 16/889,842.
PCT International Search Report, dated Oct. 1, 2020, 16 pages.

*Primary Examiner* — Elizabeth M Imani
(74) *Attorney, Agent, or Firm* — Amanda Herman Berghauer; Daniel S. Albrecht

(57) ABSTRACT

Absorbent articles containing dark-tinted nonwoven webs are provided. The dark-tinted nonwoven web may include a first plurality of filaments having a diameter between a between about 8 μm and about 50 μm, wherein the first plurality of filaments includes a pigment. The dark-tinted nonwoven web may include a second plurality of filaments having a diameter between about 0.3 μm and about 5 μm. The dark-tinted nonwoven web may have a CIE L* value of between about 0 and about 26.

16 Claims, 10 Drawing Sheets

(56) References Cited

U.S. PATENT DOCUMENTS

| | | | |
|---|---|---|---|
| 5,624,425 A * | 4/1997 | Gray | A61F 13/4942 |
| | | | 604/385.28 |
| 6,645,190 B1 | 11/2003 | Olson et al. | |
| 6,761,711 B1 | 7/2004 | Fletcher et al. | |
| 6,817,994 B2 | 11/2004 | Popp et al. | |
| 6,840,928 B2 | 1/2005 | Datta et al. | |
| 6,849,067 B2 | 2/2005 | Fletcher et al. | |
| 6,893,426 B1 | 5/2005 | Popp et al. | |
| 6,953,452 B2 | 10/2005 | Popp et al. | |
| 6,969,377 B2 | 11/2005 | Koele et al. | |
| 7,156,833 B2 | 1/2007 | Couture-Dorschner et al. | |
| 7,201,744 B2 | 4/2007 | Van Gompel et al. | |
| 7,497,851 B2 | 3/2009 | Koele et al. | |
| 7,682,349 B2 | 3/2010 | Popp et al. | |
| 7,862,550 B2 | 1/2011 | Koele et al. | |
| 7,901,393 B2 | 3/2011 | Matsuda et al. | |
| 8,007,485 B2 | 8/2011 | Popp et al. | |
| 8,361,048 B2 | 1/2013 | Kuen et al. | |
| 8,372,052 B2 | 2/2013 | Popp et al. | |
| 8,579,876 B2 | 11/2013 | Popp et al. | |
| 8,747,379 B2 | 6/2014 | Fletcher et al. | |
| 9,421,137 B2 | 8/2016 | Lavon et al. | |
| 2003/0109839 A1 | 6/2003 | Costea | |
| 2008/0132872 A1 | 6/2008 | Trennepohl | |
| 2010/0028638 A1 | 2/2010 | Reichardt | |
| 2011/0196327 A1 * | 8/2011 | Chhabra | A61F 13/4753 |
| | | | 604/385.101 |
| 2011/0319855 A1 * | 12/2011 | Lash | A61F 13/49017 |
| | | | 604/385.01 |
| 2012/0150135 A1 | 6/2012 | Tee, Jr. et al. | |
| 2013/0211363 A1 | 8/2013 | LaVon et al. | |
| 2013/0280481 A1 | 10/2013 | Mitsuno | |
| 2014/0005020 A1 | 1/2014 | LaVon et al. | |
| 2015/0164705 A1 | 6/2015 | Thomas et al. | |
| 2017/0151103 A1 * | 6/2017 | Bianchi | A61F 13/49 |
| 2019/0053551 A1 | 2/2019 | Jascomb | |
| 2020/0077722 A1 | 3/2020 | Jascomb | |
| 2020/0375812 A1 | 12/2020 | Wimalasena | |

FOREIGN PATENT DOCUMENTS

| | | |
|---|---|---|
| CN | 1539036 A | 10/2004 |
| CN | 1550603 A | 12/2004 |
| CN | 1930338 A | 3/2007 |
| CN | 102112081 A | 6/2011 |
| CN | 102753127 A | 10/2012 |
| CN | 102922796 A | 2/2013 |
| CN | 105473114 A | 4/2016 |
| CN | 205242011 U | 5/2016 |
| CN | 106393840 A | 2/2017 |
| CN | 107072840 A | 8/2017 |
| CN | 107846996 A | 3/2018 |
| CN | 108289776 A | 7/2018 |
| CN | 108697560 A | 10/2018 |
| CN | 109310541 A | 2/2019 |
| EP | 1108406 A2 | 6/2001 |
| JP | 2017160548 A | 9/2017 |
| JP | 2018117928 A | 8/2018 |
| JP | 2018141244 A | 9/2018 |
| WO | 9822056 A1 | 5/1998 |
| WO | 2017192654 A4 | 12/2017 |

* cited by examiner

DARK-TINTED NONWOVEN WEBS

CROSS REFERENCE TO RELATED APPLICATION

This application claims the benefit, under 35 U.S.C. 119(e), of U.S. Provisional Patent Application Ser. No. 62/856,454, filed Jun. 3, 2019, which is incorporated by reference in its entirety.

FIELD

The present disclosure is generally directed to absorbent articles comprising dark-tinted nonwoven webs. The dark-tinted nonwoven webs of the present disclosure may be used to form a portion of disposable absorbent articles and more particularly of premium looking disposable absorbent articles with liquid barrier properties.

BACKGROUND

Disposable absorbent articles for absorbing bodily fluids have been known for quite some time. Recently, industry has moved to make these disposable absorbent articles more aesthetically appealing. For example, delightful printing has been provided to appeal to the users of the articles. In the context of adult incontinence articles, some currently marketed products utilize tinted materials to provide aesthetically pleasing designs to users. These tinted articles often utilize a tinted material on the backsheet so that the outer surface of the article looks more like underwear. For example, on the market today, there are articles with nude colored backsheets and articles with grey colored backsheets. There are also disposable absorbent articles on the market which include printed designs on a wearer-facing surface of the article. Typically, printing is applied to a layer beneath the wearer-facing surface to minimize the likelihood of ink rubbing off on the consumer during use. Because the ink is applied beneath the wearer-facing surface, the printed designs may appear muted through the wearer-facing surface unless a very high basis weight of ink is utilized. Unfortunately, higher basis weights of inks can be cost prohibitive.

To reduce the likelihood of ink-rub-off while maintaining a more vibrant appearance, a pigment may be utilized during formation of a tinted material layer of the absorbent article. This may be especially effective when a pigment is incorporated into the masterbatch of a melt-spinnable polymer. Pigments are typically made up of a particulate material that may be suspended in the polymer masterbatch and locked in the filaments during the melt spinning process. Nonwoven webs comprising spunmelt filaments are useful in absorbent articles because they may be manufactured with filaments of varying sizes and physical characteristics. For example, small-diameter filaments may exhibit fluid barrier properties, reducing or preventing the flow of fluid, such as bodily exudates, through portions an absorbent article in areas that comprise these small diameter filaments.

The addition of pigments to a nonwoven web comprising spunmelt filaments may be problematic, however, where the desired color of the nonwoven web is a dark shade and where the filament diameters are less than about 8 micrometers, as the pigments may not disperse well in small-diameter filaments.

Based on the foregoing, nonwoven webs comprising pigments and methods of making the same should be improved.

SUMMARY

To solve the problems advanced above, the present disclosure provides dark-tinted nonwoven webs comprising both larger and smaller diameter filaments. The larger diameter filaments may efficiently incorporate pigment particles and create a pleasing dark-tinted nonwoven web. The smaller diameter filaments may provide fluid barrier properties to the nonwoven webs to at least partially slow the migration of fluids, such as bodily exudates through the nonwoven webs. The smaller diameter filaments may or may not comprise a pigment. Where the smaller diameter filaments comprise a pigment, the pigment may not be incorporated as efficiently as compared to the larger diameter filaments. The larger diameter filaments may be sufficiently numerous to overcome the reduced incorporation of pigment into the smaller diameter filaments, thus creating an overall dark-tinted nonwoven web with fluid barrier properties.

The present disclosure provides, in part, absorbent articles comprising dark-tinted nonwoven webs that comprise both larger and smaller diameter filaments. The dark-tinted nonwoven webs may comprise a first plurality of filaments having a diameter between about 8 µm and about 50 µm. The first plurality of filaments may comprise a pigment. The dark-tinted nonwoven webs may comprise a second plurality of filaments having a diameter between about 0.3 µm and about 5 µm. The dark-tinted nonwoven webs may comprise a first side and an opposing second side, wherein the first plurality of filaments comprises a portion of the first side, and wherein the first plurality of filaments comprises a portion of the second side. The dark-tinted nonwoven webs may have an L* value of between about 0 and about 26, as measured from either the first side or the second side, according to the CIE L*a*b* Test disclosed herein.

The present disclosure provides, in part, absorbent articles comprising dark-tinted nonwoven webs that comprise both larger and smaller diameter filaments. The dark-tinted nonwoven webs may comprise a first plurality of filaments having a diameter between about 8 µm and about 50 µm. The first plurality of filaments may comprise a pigment. The dark-tinted nonwoven webs may comprise a second plurality of filaments having a diameter between about 0.3 µm and about 5 µm. The second plurality of filaments may comprise a pigment. The dark-tinted nonwoven webs may comprise a first side and an opposing second side, wherein the first plurality of filaments comprises a portion of the first side, and wherein the first plurality of filaments comprises a portion of the second side. The dark-tinted nonwoven webs may have an L* value of between about 0 and about 26, as measured from either the first side or the second side, according to the CIE L*a*b* Test disclosed herein.

The present disclosure provides, in part, absorbent articles comprising dark-tinted nonwoven webs, wherein the second plurality of filaments do not comprise, or are free of, a pigment. The dark-tinted nonwoven webs may have a First Filament Ratio, wherein a number of filaments of the first plurality of filaments as measured from the first side, to the number of filaments of the first plurality of filaments as measured from the second side, is between about 1.5 to about 1 and about 4 to about 1, according to the Filament Ratio Test disclosed herein. The dark-tinted nonwoven webs may have an L* value of between about 0 and about 26, as measured from the first side, according to the CIE L*a*b* Test disclosed herein.

The present disclosure provides, in part, absorbent articles comprising dark-tinted nonwoven webs, wherein the second plurality of filaments comprise a pigment. The dark-tinted nonwoven webs may have a First Filament Ratio, wherein a number of filaments of the first plurality of filaments as measured from the first side, to the number of filaments of the first plurality of filaments as measured from the second side, is between about 1.25 to about 1 and about 3.5 to about 1, according to the Filament Ratio Test disclosed herein. The dark-tinted nonwoven webs may have an L* value of between about 0 and about 26, as measured from the first side, according to the CIE L*a*b* Test disclosed herein.

The present disclosure provides, in part, absorbent articles comprising one or more dark-tinted nonwoven webs. The one or more dark-tinted nonwoven webs may form at least a portion of, or all of, a topsheet, an acquisition layer, a secondary topsheet, a backsheet, a barrier cuff, an outer cover, and/or any other component or components thereof.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1:
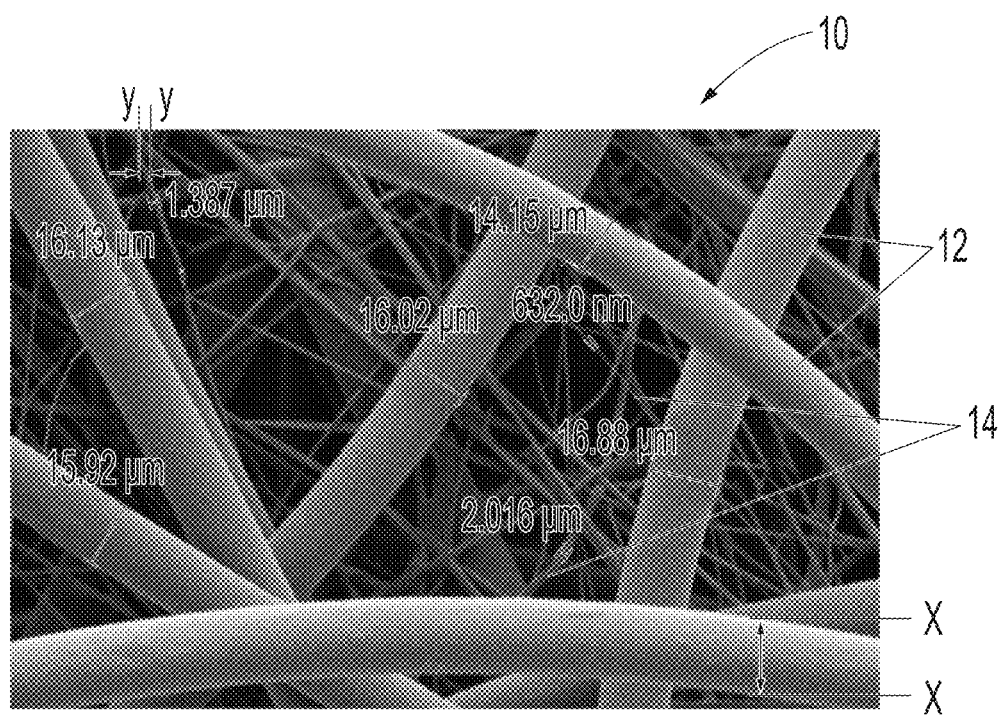
FIG. 1 is an image of a dark-tinted nonwoven web taken with Scanning Electron Microscopy (SEM) at 1,000× magnification.

Various non-limiting forms of the present disclosure will now be described to provide an overall understanding of the principles of the structure, function, manufacture, and use of dark-tinted nonwoven webs disclosed herein. One or more examples of these non-limiting forms are illustrated in the accompanying drawings. Those of ordinary skill in the art will understand that the dark-tinted nonwoven webs described herein and illustrated in the accompanying drawings are non-limiting examples. The features illustrated or described in connection with one non-limiting form may be combined with the features of other non-limiting forms. Such modifications and variations are intended to be included within the scope of the present disclosure.

The dark-tinted nonwoven webs of the present disclosure may be utilized in absorbent articles and provide barrier properties and an aesthetically pleasing effect. The dark-tinted nonwoven webs of the present disclosure may be utilized in many different areas of the absorbent article. For example, the dark-tinted nonwoven webs of the present disclosure may serve as suitable barrier components, e.g. barrier cuffs, backsheets, and the like, which may slow bodily exudate penetration through the article and/or inhibit bodily exudates from leaking from the absorbent article. As another example, the nonwoven webs of the present disclosure may be utilized as bodily exudate permeable components, e.g., topsheets, which can effectively mask staining from bodily exudate insults. As a further example, the nonwoven webs of the present disclosure may be utilized as outer covers, providing an aesthetically pleasing dark color to the outside of an absorbent article.

The inventor has found that colorant dispersion within the constituent filament material may be an important variable in achieving a desired dark color. For example, where a colorant comprises a pigment (i.e., insoluble particles in suspension), colorant dispersion within relatively small diameter filaments (e.g., less than 8 micrometers) may be impaired. Small diameter filaments, however, may be useful as they may form compact webs that inhibit bodily exudate penetration through the webs. The inventor has also found that problems associated with colorant dispersion in small diameter filaments may only be problematic where the desired color of a nonwoven web, or the absorbent article comprising such a nonwoven web, has a CIE L* value of less than about 60. For nonwoven webs with L* values of greater than 60, a lack of dispersion of colorant may not be as noticeable to the naked eye. Additionally, the inventor has found a particular challenge when the desired dark color of a nonwoven web with barrier properties has a CIE L* value of less than about 26 as measured from at least one side of the nonwoven web. A nonwoven web with a CIE L* value of less than about 26, as measured from at least one side of the nonwoven web, may be desirable, for example, in the construction of an absorbent article that may be intended to match dark-colored underwear.

As used herein, the term "Color" comprises any primary color, e.g., white, black, red, blue, violet, orange, yellow, green, and indigo as well as any declination thereof or mixture thereof. Colors can be measured according an internationally recognized 3D solid diagram of colors where all colors that are perceived by the human eye are converted into a numerical code. This system is based on three dimensions (x,y,z) and specifically L*, a*, b*. When a color is defined according to this system, L* represents lightness (0=black, 100=white), a* and b* independently each represent a two-color axis, a* representing the axis red/green (+a=red, −a=green), while b* represents the axis yellow/blue (+b—yellow, −b=blue).

As used herein, the terms "dark shade", "dark tinted", and "dark colored", refer to an absorbent article, or a portion of an absorbent article, when color tested as described herein from at least one side of the article yields an L* value of less than about 26 and an maximum absolute a* and maximum absolute b* value that may be derived from the equation (L* value)=−1.6667(max. absolute a* and b* value)+30. For example, when the L* value is 26, the maximum absolute a* and b* value may be derived from the equation 26=−1.6667 (max. absolute a* and b* value)+30. Thus, when the L* value is 26, the maximum a* and b* values is 2.4. Therefore, when the dark-tinted portion of an absorbent article has an L* value of 26, it may have a maximum a* value of 2.4 or −2.4, and a maximum b* value of 2.4 or −2.4. As another example, when the L* value of a dark-tinted absorbent article is 10, the maximum absolute a* and b* value is 12 or −12.

As used herein, the terms "fiber" and "filament" refer to any type of artificial continuous strand produced through a spinning process, a meltblowing process, a melt fibrillation or film fibrillation process, or an electrospinning production process, or any other suitable process to make filaments. The term "continuous" within the context of filaments is distinguishable from staple length fibers in that staple length fibers are cut to a specific target length. In contrast, "continuous filaments" are not cut to a predetermined length. Instead, they can break at random lengths, but are usually longer than staple length fibers.

As used herein, the terms "hydrophilic" and "hydrophobic" have meanings that are well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic may increase the contact angle of water on the surface of a material, while compositions which are hydrophilic may decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein, the term "meltblown filaments" refers to filaments or fibers which are formed by extruding molten thermoplastic material and have diameters of less than about 5 microns. For example, meltblown filaments may have a diameter between 0.3 microns to 5 microns.

As used herein, the term "nonwoven web" refers to a web having a structure of randomly oriented individual fibers or filaments which are interlaid, but not in a repeating pattern as in a woven or knitted fabric. The basis weight of nonwoven fabrics is usually expressed in grams per square meter (gsm). The basis weight of nonwoven webs suitable for use in the articles of the present disclosure may range from about 8 gsm to about 75 gsm, depending on the ultimate use of the nonwoven webs. For example, where the nonwoven webs disclosed herein are utilized as topsheets, the basis weight of the material web may be between about 8 gsm and about 50 gsm, between about 14 gsm and about 45 gsm, or between 20 gsm and about 40 gsm.

All ranges disclosed herein specifically recite all 0.1 increments within the specified ranges and all ranges formed therein or thereby.

Nonwoven Webs

Nonwoven webs are useful in many fields, such as the hygiene field, the dusting and cleaning implement field, and the medical field, for example. In the hygiene filed, nonwoven webs may be used in the absorbent article field, for example as components in pad-style articles such as adult incontinence pads, panty liners, sanitary napkins, absorbent pads, bed pads, and various other products. Additionally, in the absorbent article field, nonwoven webs may be used as components in taped and pant-style articles, such as adult incontinence pants, training pants, and taped diapers. Nonwoven webs may be used in absorbent articles as topsheets, backsheets, barrier cuffs, outer covers, and core wrap materials, for example. The dark-tinted nonwoven webs of the present disclosure may have particular application as a topsheet, outer cover, and/or barrier cuff nonwoven material.

Filament Composition and Formation

Dark-tinted nonwoven webs of the present disclosure may comprise filaments made by a spunmelt process. Briefly, the term "spunmelt" refers to a process of forming a nonwoven web from thin, continuous filaments produced by extruding molten polymers, for example thermoplastics, from orifices of a plate known as a spinneret or die. The continuous filaments are drawn as they cool. Spunmelt technologies may comprise both the meltblowing process and spunbonding processes. A spunbonding process may comprise supplying a molten polymer, which is then extruded under pressure through a large number of orifices in a plate known as a spinneret or die. The resulting continuous filaments are quenched and drawn by any of a number of methods. In the spunbonding process, the continuous filaments are collected as a loose nonwoven web upon a moving surface, such as a wire mesh conveyor belt, for example. The loose nonwoven web may be point bonded, where small points of a nonwoven web may be subjected to localized heating and/or localized pressure to consolidate the fibers of the nonwoven web to hold the web structure together. Spunbond filaments are generally continuous and may have a filament diameter larger than 8 microns. For example, spunbond filaments may have filament diameters between about 8 microns and about 50 microns. Spunbond filaments are herein designated as "spunbond" or "S" filaments.

Dark-tinted nonwoven webs of the present disclosure may comprise filaments made by a meltblowing process. The meltblowing process is related to the spunbonding process for forming filaments, in that a molten polymer is extruded under pressure through orifices in a spinneret or a die. In the meltblowing process, high velocity gas impinges upon and attenuates the filaments as they exit the die. The energy of this step is such that the formed filaments are greatly reduced in diameter as compared to those of the spunbonding process, and the filaments may be fractured so that microfilaments of indeterminate length are produced. Coaxial meltblown is known in the art and is considered a form of meltblowing. Meltblown filaments may also be collected as a loose web nonwoven web and point bonded. Meltblown filaments may have diameters of less than about 5 microns. For example, meltblown filaments may have a diameter between about 0.3 microns to about 5 microns. Meltblown filaments are herein designated as "meltblown" or "M" filaments.

The filaments of dark-tinted nonwoven webs of the present disclosure may comprise mono-component or multi-component filaments, such as bi-component filaments or tri-component filaments, for example. Multi-component filaments, as used herein, means filaments comprising more than one chemical species or material (i.e., multi-constituent fibers). The filaments may comprise petroleum sourced resins, recycled resins, or bio-sourced resins, such as polylactic acid from Nature Works and polyethylene from Braskem. The filaments may have round, triangular, trilobal, or otherwise shaped cross-sections, for example. Often, the different polymer components have different melting temperatures, viscosities, glass transition temperatures, crystallinities, and/or crystallization rates. The multi-component filaments, such as bi-component filaments, may comprise sheath/core, side-by-side, islands in the sea, and/or eccentric configurations or may have other configurations.

Nonwoven Web Formation

One or more spinnerets may be used to form a dark-tinted nonwoven web. When more than one spinneret is used, the spinnerets may lay filaments down simultaneously, or in an in-line format where one spinneret is places after another along a conveyor belt. In an in-line process for forming a dark-tinted nonwoven web, the subsequent nonwoven component or components may be collected upon the surface of the previously formed nonwoven component, forming layers. Each layer may comprise filaments made by one process (e.g. spunbond, meltblown), or each layer may be made by a different process. When viewed from one side of the nonwoven web under magnification, for example using light microscopy, the layers may not be distinguishable. Filaments of varying size, however, may be distinguishable using the Filament Size Test as disclosed herein, and may allow for distinction between filaments formed, for example, by meltblown techniques versus filaments formed by spunbond techniques.

Meltblown nonwoven fiament layers may be added to spunbond nonwoven filament layers to form, for example, spunbond-meltblown ("SM") webs or spunbond-meltblown-spunbond ("SMS") webs, which may be strong webs with some liquid barrier properties. The barrier properties of meltblown filaments may be due to the ability of the filaments to pack tightly together due to their small diameter, thus forming an effective barrier to liquid permeation. When utilized in the nonwoven web of the present disclosure, meltblown filaments may reduce or inhibit the flow of fluid insults, for example bodily exudates, through the nonwoven web. This may be desirable when the nonwoven web is utilized as a barrier element of an absorbent article, for example as a barrier cuff. Liquid barrier properties of a dark-tinted nonwoven web may be assessed by the Hydrohead Value according to the Hydrostatic Head Test disclosed herein. Dark-tinted nonwoven webs of the present disclosure may have a Hydrohead Value of between about 15 mbar and about 50 mbar, between about 15 mbar and about 45 mbar, between about 17 mbar and about 40 mbar, between about 19 mbar and about 35 mbar, between about 19 mbar and about 30 mbar, or between about 21 mbar and about 30 mbar, specifically including all values within these ranges and any ranges created thereby.

FIG. 1 presents an image of a dark-tinted nonwoven web taken by scanning electron microscopy. The dark-tinted nonwoven web 10 may comprise a first plurality of filaments 12 having a diameter between about 8 µm and about 50 µm. The dark-tinted nonwoven web 10 may also comprise a second plurality of filaments 14 having a diameter between about 0.3 µm and about 5 µm.

Dark-tinted nonwoven webs of the present disclosure may comprise filaments laid down in a sided or asymmetrical manner. For example, a dark-tinted nonwoven web comprising multiple layers may comprise spunbond and meltblown webs in the form SSMS, SMSS, SSSMMS, SSMMMS, SSMMMSSS, SSSMSS, and the like. As discussed, when viewed using, for example, light microscopy, distinct layers that comprise a nonwoven web may not be distinguishable. Sided nonwoven webs may be identified, however, by following the Filament Ratio Test disclosed herein. Briefly, a first side and a second side of a dark-tinted nonwoven web are viewed using Scanning Electron Microscopy. The density of filaments with diameters between about 8 µm and about 50 µm (spunbond filaments) is measured by counting the filaments on each side of a nonwoven web. A sided nonwoven web may have a greater density of spunbond filaments on a first side of a nonwoven web as compared to a second side of a nonwoven web. Where spunbond filaments are capable of being measured and counted by viewing a side of a nonwoven web, the spunbond filaments may be said to form a portion of that side of the nonwoven web.

Figure 2:
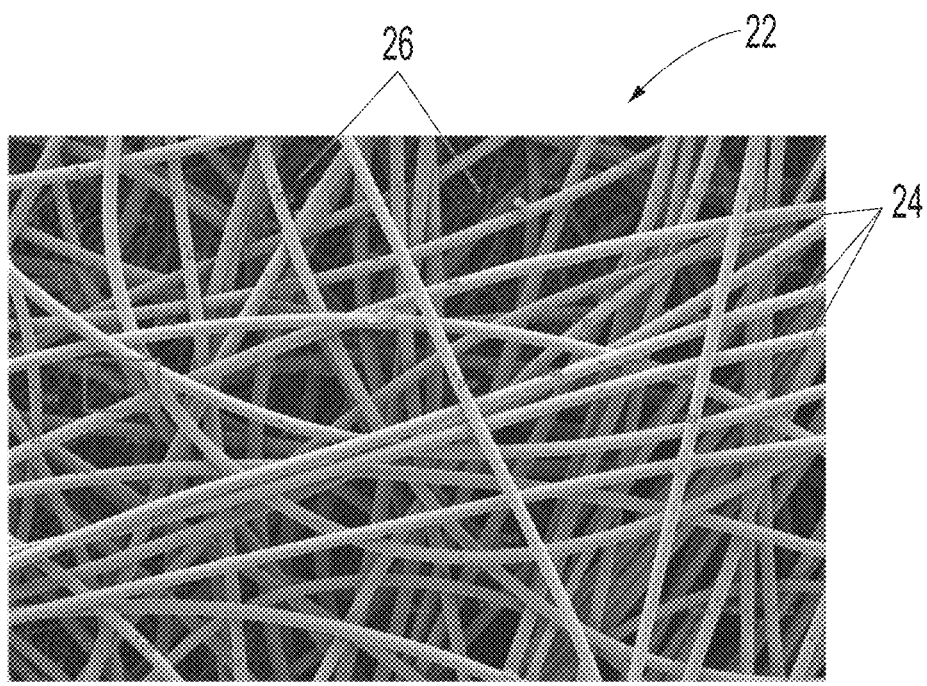
FIG. 2 is an image of a dark-tinted nonwoven web taken from a first side of the nonwoven web, using SEM at 200× magnification.
Figure 3:
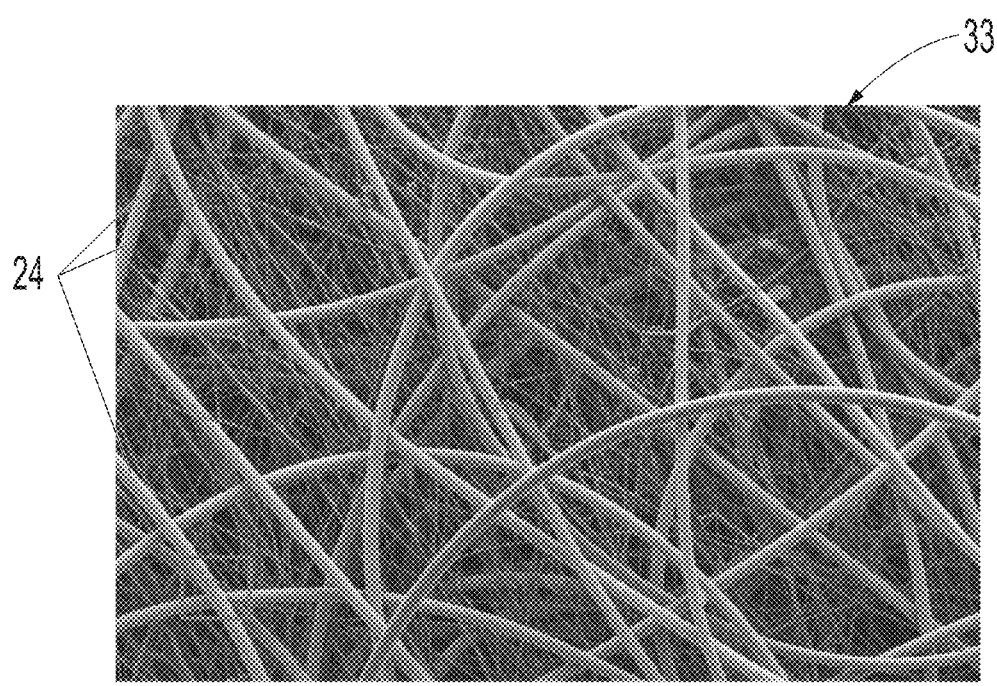
FIG. 3 is an image of a nonwoven web of the present disclosure taken from a second side of the nonwoven web, using SEM at 200× magnification.

FIGS. 2 and 3 are scanning electron microscopy images of a first side 22 and a second side 33, respectively, of a dark-tinted nonwoven web of the configuration SSMMS. In this context, the first side refers to the SS side of the dark-tinted nonwoven web, and the second side refers to the S side of the dark-tinted nonwoven web. Referring to FIG. 2, the dark-tinted nonwoven web may comprise a first side 22, a first plurality of filaments 24, and a second plurality of filaments 26. The nonwoven web may comprise a first plurality of filaments 24 having a diameter between about 8 µm and about 50 µm, and a second plurality of filaments 26 having a diameter between about 0.3 µm and about 5 µm. When viewed from the first side 22 of the nonwoven web 20, as in FIG. 2, the number of filaments comprising the first plurality of filaments 24 may be counted. The first plurality of filaments 24 may be counted according to the Filament Size Test disclosed herein.

Referring to FIG. 3, when viewed from a second side 33 of the dark-tinted nonwoven web 20, the number of filaments comprising the first plurality of filaments 24 may be counted. The first plurality of filaments 24 may be counted according to the Filament Size Test disclosed herein. A First Filament Ratio of the number of filaments of a first plurality of filaments 24 as measured from a first side 22 of a dark-tinted nonwoven web 20 to the number of filaments of a first plurality of filaments 24 as measured from a second side 33 of a dark-tinted nonwoven web 20 may be between about 1.5 to 1 and about 4 to 1, between about 1.5 to 1 and about 3.75 to 1, between about 1.75 to 1 and about 3.5 to 1, or between about 2 to 1 and about 3.25 to 1, specifically including all values within these ranges and any ranges created thereby. A First Filament Ratio may be established according to the Filament Ratio Test disclosed herein.

Dark-tinted nonwoven webs of the present disclosure may comprise a first plurality of filaments having a diameter between about 8 µm and about 50 µm. The dark-tinted webs of the present disclosure may comprise a second plurality of filaments having a diameter between about 0.3 µm and about 5 µm. The dark-tinted nonwoven webs may comprise a first side and an opposing second side. The first plurality of filaments may comprise a portion of both the first side and the second side of the dark-tinted nonwoven web.

Pigments

The dark-tinted nonwoven webs of the present disclosure may comprise a colorant which may be used in disposable absorbent articles that are worn by consumers. Such a dark-tinted nonwoven web may be used to manufacture portions of an absorbent article that are consumer pleasing and premium looking. The dark-tinted nonwoven web utilizing a colorant may have an L* value, as measured from at least one side of the nonwoven web, of between about 0 and about 26, between about 0 and about 24, between about 0 and about 22, between about 0 and about 20, or between about 0 and about 18, specifically including all values within these ranges and any ranges created thereby, according to the CIE L*a*b* Test described herein.

The use of pigments as colorants in nonwoven webs may provide certain advantages, such as preventing colorant from rubbing off on a wearer Generally, pigments may be added to a polymer masterbatch prior to filament formation. For nonwoven webs that are formed via a spunmelt process, e.g. spunbond, meltblown, etc., polymeric material is extruded through a plurality of holes in a die. Therefore, the pigment must pass through the holes in the die along with the polymeric material. The colorant may thus be locked in the polymer matrix of the filament. The inventor has found that where the colorant comprises a pigment, i.e. insoluble particles in suspension, colorant dispersion within relatively small diameter filaments, e.g. meltblown filaments with diameters of less than about 5 μm, may be difficult. Meltblown filaments are useful, however, to provide liquid barrier properties to a nonwoven web. Thus, the inventor has found that creating dark-tinted nonwoven web with liquid barrier properties to be challenging.

The inventor, however, has also found that issues associated with colorant dispersion in small diameter filaments may only be problematic where the desired color of resultant absorbent article, or nonwoven portion thereof, has an L* value of less than about 60. For L* values of greater than 60, a lack of dispersion of colorant may not be as noticeable to the naked eye. Without wishing to be bound by theory, it is believed that inadequate dispersion of pigment in a filament with a diameter less than about 8 μm may cause the filament to maintain a relatively high L* value. This may result in a nonwoven web with an overall appearance light appearance or may result in a nonwoven web with a blotchy appearance—with some areas of the web having a light appearance and other areas having a darker appearance. When the desired color of the resultant absorbent article, or nonwoven portion thereof, has an L* value of greater than about 60, the inadequate dispersion of pigment in a filament may be less impactful. The issues associated with poor dispersibility of colorant may be even more noticeable in dark-tinted nonwoven webs with a desired L* value of less than about 30. Such dark-tinted nonwoven webs may be desirable, for example, in the manufacture of absorbent articles that match or mimic dark-colored undergarments.

As discussed, pigment dispersion may be inhibited in small diameter filaments, i.e. meltblown filaments with a diameter of less than about 5 μm. Meltblown filaments, however, may provide desired liquid barrier properties to a nonwoven web. The inventor has found that, to provide a premium-looking absorbent article comprising a dark-tinted nonwoven web with barrier properties, the larger diameter filaments (for example, spunbond filaments) may comprise pigment and may be present in such a density as to sufficiently cover smaller diameter filaments that either do not comprise colorant or comprise colorant that is not sufficiently dispersed throughout the filament. Additionally, the inventor has found that a sided dark-tinted nonwoven web, where one side of the web comprises a higher density of larger diameter (i.e. spunbond) filaments, may provide a desired premium-looking absorbent article at a lower cost. Since only one side, preferably a consumer-facing side, of a nonwoven web may have a higher density of larger diameter filaments, the cost of the nonwoven web may be decreased while still providing the benefit of a premium-looking dark-tinted product with liquid barrier properties. Where the nonwoven web is not sided, both sides of a dark-tinted nonwoven web may have a CIE L* value of between about 0 and about 26. Where the nonwoven web is sided, at least one side of a dark-tinted nonwoven web have a CIE L* value of between about 0 and about 26, while the other side may have a CIE L* value of between about 0 and about 50.

Figure 4:
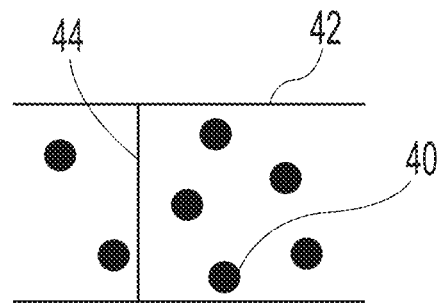
FIG. 4 is an example cross-sectional illustration of a spunbond filament.
Figure 5:
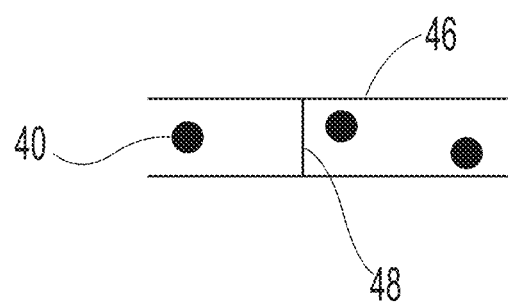
FIG. 5 is an example cross-sectional illustration of a meltblown filament.

FIG. 4 is an exemplary cross-sectional illustration of a spunbond filament. FIG. 5 is an exemplary cross-sectional illustration of a meltblown filament. It is believed that colorant particles 40 are more prevalent in the filaments 42 of the first plurality of filaments, e.g. spunbond filaments, than the filaments 46 of the second plurality of filaments, e.g. meltblown filaments. It is further believed that, because the spunbond filaments 42 have a greater diameter 44 as compared to the meltblown filaments 46, the particles 40 of the colorant have more room to distribute in the polymer matrix of the spunbond filaments 42 of the first plurality of filaments. The room to distribute may allow for much better distribution of the colorant particles 40 within the polymer matrix of the fibers and/or filaments 42 of the first plurality of filaments. The better distribution may allow for the appearance of a darker color in the fibers and/or filaments 42 of the first plurality of filaments.

In contrast, due to the smaller diameter 48 of the filaments 46 of the second plurality of filaments, e.g. meltblown filaments, the colorant particles 40 do not have as much room to distribute within the polymer matrix of the filaments of the meltblown filaments 46. It is therefore believed that the distribution of the particles 40 within the polymer matrix of the meltblown filaments 46 is much more uniform and allows substantial gaps between the colorant particles 40. It is believed that these substantial gaps allow for light to penetrate and transmit through the meltblown filaments. This results in a much lighter appearance for the fibers and/or filaments 46 of the second plurality of filaments.

Some colorants may comprise particles having sizes ranging from 8 nm to about 100 nm. However, these particles may bond together to form aggregates which may be much larger than their particle constituents. These aggregates may often be about one half the diameter of a meltblown filament, e.g. 0.3 μm to 5 μm diameter filament. Where the size of the aggregate is near one half of the diameter of the filament, the filament may be subject to easier breakage which may in turn lead to process outages and downtime. Additionally, due to the size of the particles and aggregates of the colorant, it is believed that the colorant may not disperse within smaller diameter filaments, e.g. meltblown, as easily as in larger diameter, e.g. spunbond, filaments. It is believed that a ratio of colorant particle diameter to filament diameter should be less than about 0.07, less than about 0.05, or less than about 0.04.

The utilization of smaller colorant particles may be beneficial. The use of smaller colorant particles may reduce the likelihood of die clogging as the particles pass through the spinneret die during filament formation. The use of finer colorant particles in smaller diameter (i.e. meltblown) filaments may improve colorant particle distribution within the filament, leading to the overall darker appearance of a nonwoven web comprising such filaments. Meltblown filaments comprising smaller colorant particles may also be used to form a portion of a nonwoven web and may be utilized in conjunction with basis weight manipulation of larger diameter (i.e. spunbond) filaments of the nonwoven web. The utilization of finer colorant particles may also allow for higher colorant loads to be utilized in the masterbatch. For example, finer colorant particles may be present in a masterbatch formulation of meltblown and/or spunbond filaments at about 0.25 percent by weight to about 8 percent by weight, about 0.5 percent by weight to about 6 percent by weight, about 0.75 percent by weight to about 5 percent by weight, about 1 percent by weight to about 4.5 percent by weight, about 1.25 percent by weight to about 4 percent by weight, or about 1.5 percent by weight to about 3.5 percent by weight, specifically reciting all values within these ranges and any ranges created thereby.

Additionally, the melt flow rate of the constituent chemistries of the filaments may also inhibit dispersion of the colorant particles into the polymer matrix. In general, a masterbatch is created for a particular fiber and/or filament resin. The masterbatch typically includes the colorants and other processing aids. For the creation of filaments, the masterbatch is combined with the filament resin and processed as desired. Regarding the spunbond or meltblown process, the melt flow rate of the masterbatch should be higher than the melt flow rate for the filament resin. This may ensure good dispersion of the masterbatch within the filament polymer matrix.

In some countries, colorants may be regulated, as for example, via the U.S. Code of Federal Regulations 21 CFR Part 74, Subpart D—Medical Devices or by the European Commission, to ensure they are of high purity and suitable for use against or near the body of a user. In the context of an absorbent article, the colorant used in the manufacture of a dark-tinted nonwoven web may be a high purity colorant or high purity pigment. As used herein, the term "high purity" refers to a colorant or pigment that meets the following criteria:

(1) Surface area by nitrogen BET (Brunauer, Emmett, Teller) method, 50 to 260 m$^2$/gram.

(2) Weight loss on heating at 950° C. for 7 minutes (predried for 1 hour at 125° C.), not more than 2 percent.

(3) Ash content, not more than 0.15 percent.

(4) Arsenic (total), not more than 3 milligrams per kilogram (mg/kg) (3 parts per million).

(5) Lead (total), not more than 10 mg/kg (10 parts per million).

(6) Mercury (total), not more than 1 mg/kg (1 part per million).

(7) Total sulfur, not more than 0.65 percent.

(8) Total polycyclic aromatic hydrocarbons (PAHs), not more than 0.5 mg/kg (500 parts per billion).

(9) Benzo[a]pyrene, not more than 0.005 mg/kg (5 parts per billion).

(10) Dibenz[a,h]anthracene, not more than 0.005 mg/kg (5 parts per billion).

(11) Total color (as carbon), not less than 95 percent.

Absorbent articles of the present disclosure comprising dark-tinted nonwoven webs may comprise high purity pigments. The dark-tinted nonwoven webs of the present disclosure may comprise a first plurality of filaments having a diameter between about 8 μm and about 50 μm, wherein the first plurality of filaments comprises a high purity pigment. The dark-tinted nonwoven webs of the present disclosure may comprise a second plurality of filaments having a diameter between about 0.3 μm and about 5 μm, wherein the second plurality of filaments may or may not comprise a high purity pigment. The dark-tinted nonwoven webs of the present invention may have an L* value of less than 26 as measured from at least one side of the nonwoven web, which may create an aesthetically pleasing appearance which may more closely match a user's undergarments. The dark-tinted nonwoven webs of the present disclosure may form at least a portion of an absorbent article.

The absorbent articles of the present disclosure comprising dark-tinted nonwoven webs may comprise a first plurality of filaments having a diameter between about 8 μm and about 50 μm. The first plurality of filaments may comprise a pigment. The first plurality of filaments may be spunbond filaments. The nonwoven web may comprise a second plurality of filaments having a diameter between about 0.3 μm and about 5 μm, wherein the second plurality of filaments does not comprise a pigment. The second plurality of filaments may be meltblown. The dark-tinted nonwoven webs may have an L* value of less than 26 as measured from at least one side of the nonwoven web.

The dark-tinted nonwoven web may be sided, meaning the nonwoven web may have a greater density of first filaments (larger-diameter filaments) on a first side of a nonwoven web as compared to a second side. Where the second plurality of filaments (e.g. meltblown filaments) do not comprise a pigment, the sided nature of the nonwoven web may be particularly beneficial. For example, where one side, for example the first side, of a nonwoven web incorporated into an absorbent article faces outward from the article while the second side faces inward, the sided nature of the nonwoven web may allow a first side of the nonwoven web to present a premium, dark-tinted web with an L* value of between about 0 and about 26. The second, inward facing side, may have a lower density of pigment-containing spunbond filaments and therefore may present a lighter-tinted nonwoven web. Such a sided nonwoven web may be more cost effective in providing a premium dark-tinted nonwoven web as a component of an absorbent article because the second, inward facing side of the nonwoven web has a lower basis weight and thus requires less material.

Sidedness may be shown by calculating a First Filament Ratio according to the Filament Ratio Test disclosed herein. Briefly, the number of filaments of the first plurality of filaments may be measured from a first side of a nonwoven web. Next, the number of filaments of the first plurality of filaments may be measured from an opposing second side of the nonwoven web. A ratio of the number of filaments as measured from the first side versus filaments as measured from the second side may then be constructed. Dark-tinted nonwoven webs of the present disclosure may have a First Filament Ratio of between about 1.25 to 1 and about 4 to 1, between about 1.5 to 1 and about 3.75 to 1, between about 1.75 to 1 and about 3.5 to 1, or between about 2 to 1 and about 3.5 to 1, specifically reciting all values within these ranges and any ranges created thereby, according to the Filament Ratio Test. Where the second plurality of filaments do not comprise a pigment, the First Filament Ratio may be higher, for example between about 1.5 to 1 and 4 to 1, between about 2 to 1 and about 3.75 to 1, or between about 2.5 to 1 and about 3.5 to 1, specifically reciting all values within these ranges and any ranges created thereby. A higher First Filament Ratio may be needed in such a case in order to sufficiently mask the light colored second plurality of filaments and create an overall dark-tinted nonwoven web with an L* value of between about 0 and about 26, as measured from either a first side or a second side of the nonwoven web. Where the second plurality of filaments comprises a pigment, the First Filament Ratio may be lower, for example between about 1.25 to 1 and 3.5 to 1, between about 1.5 to 1 and about 3.25 to 1, or between about 2 to 1 and about 3 to 1, specifically reciting all values within these ranges and any ranges created thereby. In such a case, a lower density of the first plurality of filaments may be sufficient to create a dark-tinted nonwoven web with an L* value of between about 0 and about 26, between about 5 and 26, between about 8 and 23, between about 8 and 20, or between about 10 and 18, specifically reciting all values within these ranges and any ranges created thereby, because the second plurality of filaments may assist in providing a dark color.

The first plurality of filaments may have a basis weight of between about 2 gsm and about 50 gsm, between about 4 gsm and about 25 gsm, between about 5 gsm and about 20 gsm, between about 8 gsm and about 17 gsm, specifically reciting all values within these ranges and any ranges created thereby. Higher basis weights, for example, about 12 gsm, about 14 gsm, about 16 gsm, about 18 gsm, about 20 gsm, about 22 gsm, and about 24 gsm, may be utilized and are believed to provide a more even distribution of the first plurality of filaments. The more even distribution of the first plurality of filaments is believed to effectively mask the second plurality of filaments. So, even without the desired coloration of the second plurality of filaments, the first plurality of filaments may effectively hide the second plurality of filaments such that the non-color or different color does not show through the first plurality of filaments to such an extent to distort the overall color of the nonwoven web. In such a construction, the first side may form a wearer-facing surface of an absorbent article.

The absorbent articles comprising dark-tinted nonwoven webs of the present disclosure may comprise a first plurality of filaments having a diameter between about 8 μm and about 50 μm. The first plurality of filaments may comprise a pigment. The first plurality of filaments may be spunbond filaments. The nonwoven web may comprise a second plurality of filaments having a diameter between about 0.3 μm and about 5 μm. The second plurality of filaments may comprise a pigment. The second plurality of filaments may be meltblown. The dark-tinted nonwoven webs may comprise a first side and an opposing second side, wherein the first plurality of filaments comprise a portion of the first side and wherein the first plurality of filaments comprise a portion of the second side. The dark-tinted nonwoven web may have an L* value of between about 0 and about 26 as measured from either the first or the second side, according to the CIE L*a*b* Test described herein.

In addition to or independently of the increase in basis weight of the first plurality of filaments to create a sided nonwoven web, the basis weight of the second plurality of filaments may be reduced. For example, the basis weight of the second plurality of filaments may be between about 0.1 gsm to about 10 gsm, about 0.2 gsm to about 5 gsm, about 0.5 gsm to about 3 gsm, or about 1 gsm to about 1.5 gsm, specifically reciting all values within these ranges and any range created thereby. It is believed that by reducing the basis weight of the second plurality of filaments (i.e. the small diameter filaments), the appearance of fibers and/or filaments which are not in accordance with the desired color specification are less noticeable. However, where a liquid barrier material is desired, care should be taken to ensure that the desired barrier properties are achieved. Lower basis weights of the second plurality of filaments may reduce the liquid barrier properties of the overall nonwoven web. In such constructions, the basis weight of the first plurality of filaments may be about 21 gsm, about 18 gsm, about 16 gsm or about 14 gsm.

In conjunction with the increase in basis weight of the first plurality of filaments, the decrease in basis weight of the second plurality of filaments, or independently thereof, the second plurality of filaments may comprise a colorant which is different than the colorant in the first plurality of filaments. For example, finer size colorant particles for the filaments of the second plurality of filaments may be utilized as compared to those utilized for the first plurality of filaments. It is contemplated where a first colorant for the first plurality of filaments is a first color and a second colorant for the second plurality of filaments is a second color, wherein the first color and the second color are different. Or, the first colorant and the second colorant may be the same color. In such constructions, the second colorant may comprise an average particle size which is less than that of the first colorant. The smaller average particle size can be beneficial in providing better dispersion of the colorant particles through the polymer matrix of the filaments of the second plurality of filaments.

Absorbent Article
Pad-Style Articles

The dark-tinted nonwoven webs of the present disclosure may form a nonwoven portion of a pad-style absorbent article. A pad-style absorbent article may be useful, for example, as a panty liner or adult incontinence pad for the absorption of body exudates, such as menses or blood, vaginal discharges, and/or urine. When incorporated into an absorbent article, the dark-tinted nonwoven webs may provide liquid barrier properties and a pleasing dark color that may be safe to position against a wearers skin. The nonwoven webs of the present disclosure may be utilized in many different areas of an absorbent article. For example, the nonwoven webs of the present disclosure may serve as suitable barrier components, e.g. barrier cuffs, backsheets, which can inhibit liquid from leaking from the absorbent article. As another example, the nonwoven webs of the present disclosure may be utilized as liquid permeable components, e.g. apertured topsheets, which can effectively mask staining from liquid insults.

Figure 6:
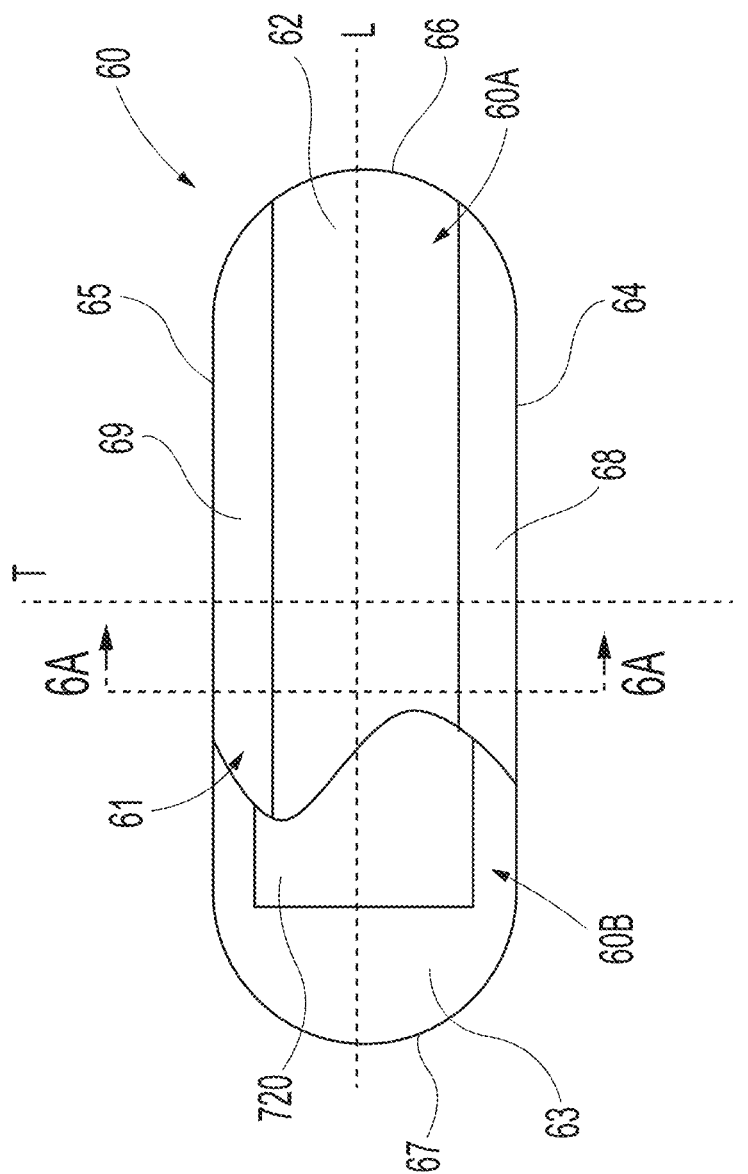
FIG. 6 is a plan view of an absorbent article.

A plan view of an exemplary pad-style absorbent article in accordance with the present disclosure is provided in FIG. 6. As shown, an absorbent article 60 may comprise a chassis 61. The chassis 61 may comprise a topsheet 62, a backsheet 63, and an absorbent core 720 disposed between the topsheet 62 and the backsheet 63. The absorbent article 60 may further comprise a wearer-facing surface 60A and an opposing garment-facing surface 60B. The topsheet 62 may form at least a portion of the wearer-facing surface 60A and the backsheet 63 may form at least a portion of the garment-facing surface 60B.

The pad-style absorbent article 60 may further comprise a longitudinal axis L and a transverse axis T which may be perpendicular to the longitudinal axis L and in the same plane as the absorbent article in a flattened state. A pair of longitudinal edges 64 and 65 may extend generally parallel to the longitudinal axis L. A pair of end edges 66 and 67 may extend generally parallel to the transverse axis and connect the longitudinal edges on opposite ends of the absorbent article 60.

The pad-style absorbent article 60 may further comprise a pair of barrier cuffs, 68 and 69 which may extend generally parallel to the longitudinal axis L. As shown, the barrier cuffs 68 and 69 may be disposed adjacent the longitudinal edges 64 and 65, respectively. The dark-tinted nonwoven webs of the present disclosure may form a nonwoven portion of one or both barrier cuffs.

Figure 7:
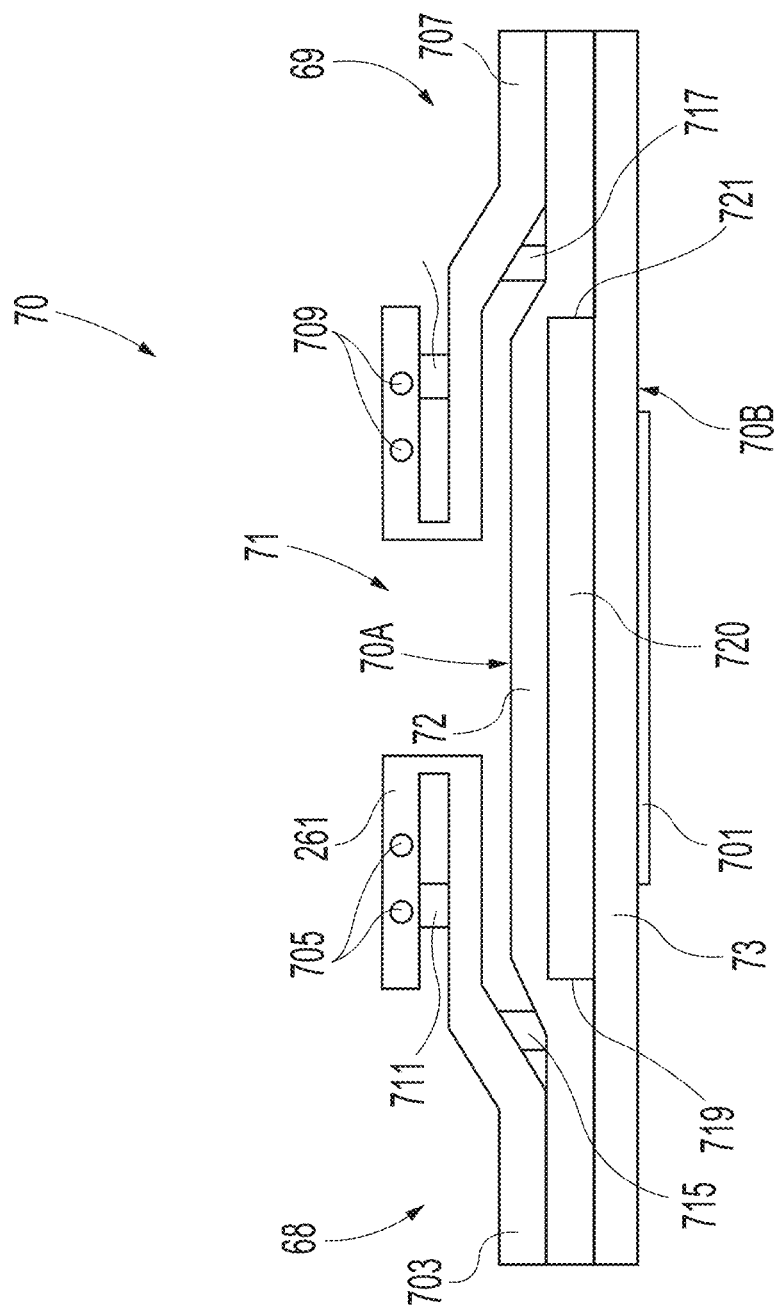
FIG. 7 is a cross-sectional view of the pad-type absorbent article of FIG. 6, taken about line 6A-6A.

FIG. 7 is a cross-sectional view of the pad-style absorbent article of FIG. 6, taken at line 6A-6A. Regarding FIG. 7, the absorbent article 60 may comprise a first barrier cuff 68 and a second barrier cuff 69 and fastening adhesive 701 disposed on a garment-facing surface 60B of the absorbent article 60. The first barrier cuff 68 and the second barrier cuff 69 may be attached to the absorbent article in any suitable location. For example, as shown, the first barrier cuff 68 and the second barrier cuff 69 may be attached to a wearer-facing surface 60A. As shown, the first barrier cuff 68 and the second barrier cuff 69 are attached to the topsheet 72. In some forms, the first barrier cuff 68 and the second barrier cuff 69 may be attached to a garment-facing surface 60B of the chassis 71. For example, the first barrier cuff 68 and the second barrier cuff 69 may be attached to the backsheet 73.

As shown, in some forms, the first barrier cuff 68 comprises a first cover 703 and a first elastic member 705. The second barrier cuff 69 comprises a second cover 707 and a second elastic member 709. As shown, the first cover 703 may fully enclose the first elastic member 705. Similarly, the second cover 707 may fully enclose the second elastic member 709.

While the first barrier cuff 68 and the second barrier cuff 69 are shown as discrete elements which are attached to the chassis 71, any suitable configuration may be utilized. For example, the first cover 703 and/or the second cover 707 may comprise a portion of the topsheet 72 and/or a portion of the backsheet 73. In such forms, the first barrier cuff 68 and/or the second barrier cuff 69 may be integrally formed with the chassis 71.

Referring again to FIG. 7, the first elastic member 705 and the second elastic member 709 may be attached to the first cover 703 and the second cover 707, respectively, by any suitable means. In one example, the first elastic member 705 may be adhesively attached to the first cover 703. Similarly, the second elastic member 709 may be adhesively attached to the second cover 707. For example, as shown, first adhesive portions 711 and 713 may attach the elastic members 705 and 709 to their respective covers 703 and 707. Similarly, second adhesive portions 715 and 717 may attach their respective covers 703 and 707 to the topsheet 72. The first elastic member 705 and the second elastic member 709 may be attached in only a portion of the first cover 703 and second cover 707, respectively. Additional forms are contemplated where the first elastic member 705 and/or the second elastic member 709 are attached to the chassis 71 in conjunction with or independently from their respective covers 703 and 707.

The elastic members 705 and 709 may be disposed laterally inboard of side edges 719 and 721 of the absorbent core 720. In other forms, the elastic members 705 and 709 may be disposed laterally outboard of the side edges 719 and 721 of the absorbent core 720. The elastic members of the barrier cuffs may be attached with glue, using various glue lengths, various glues, and various glue amounts and placements.

Minimum spacing between the first barrier cuff 68 and the second barrier cuff 69 may be largely driven by female anatomy. However, tradeoffs can occur where the barrier cuffs (and their respective elastic members) are disposed too far outboard of the absorbent core 720 and too far inboard of the absorbent core 720. As such, spacing between the most distal elastic members of their respective barrier cuffs should be carefully selected. Starting from the narrowest width, spacing between the most distal elastic members of the first barrier cuff 68 and the second barrier cuff 69 should be large enough to allow sufficient access to the absorbent core 720 during use, while also taking into account the forces which will be applied to the pad. If too narrow, access to a portion of the absorbent core 720 could be obstructed which could lead to leakage despite the barrier cuffs 68 and 69. In some forms of the present invention, minimum spacing between the elastic member of the first barrier cuff 68 and the elastic member of the second barrier cuff 69 which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Taped and Pant-Style Absorbent Articles

Figure 8:
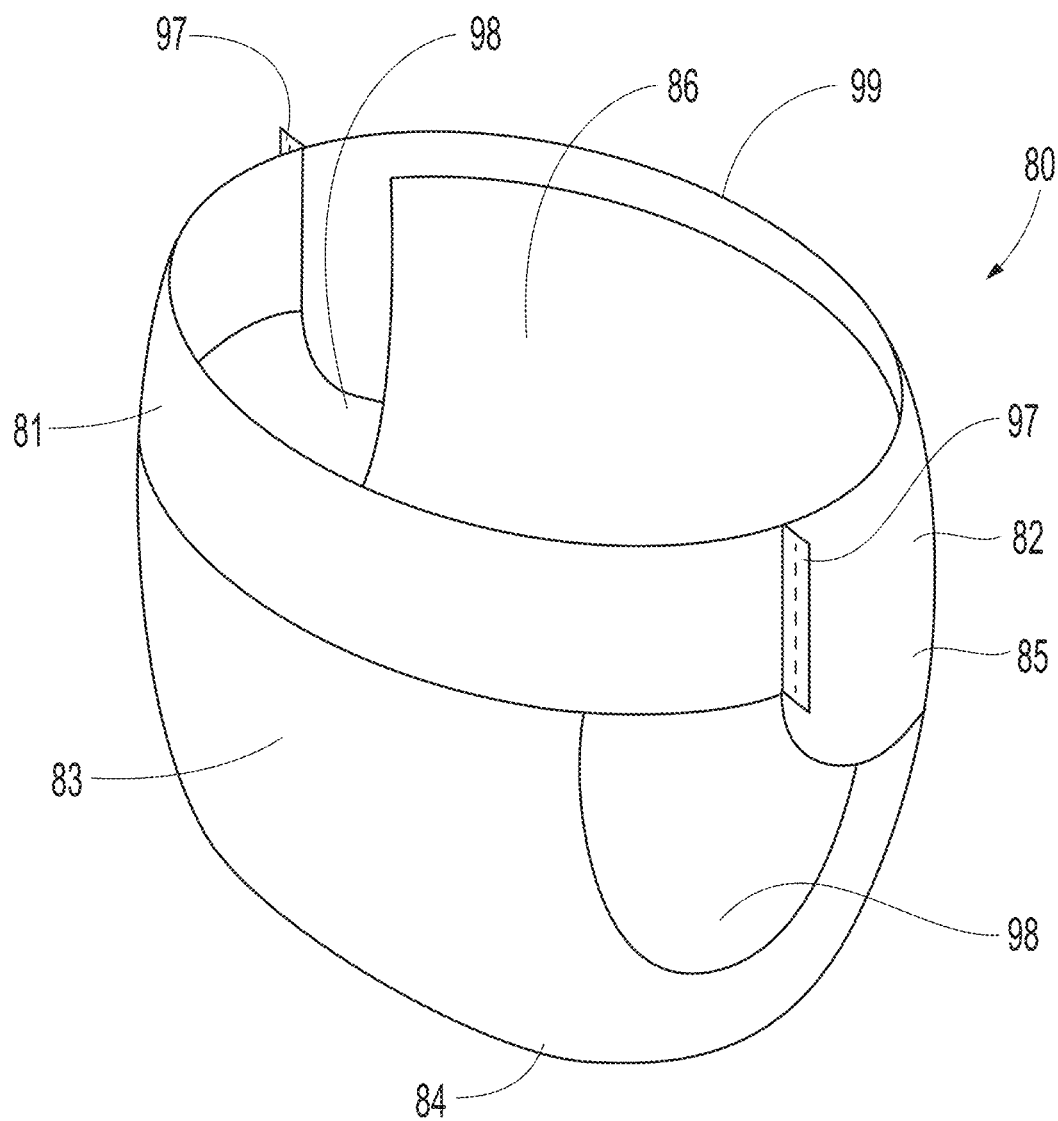
FIG. 8 is a front perspective view of a pant-style absorbent article.

The dark-tinted nonwoven webs of the present disclosure may form a nonwoven portion of a taped and/or pant-style absorbent article. Taped and pant-style absorbent articles may be configured to be worn around the waist and lower torso of a wearer. Pant configuration absorbent articles are typically packaged with front and rear side or hip panels fastened or seamed together such that the product resembles a pair of briefs or underwear as depicted in FIG. 8. These are typically marketed for wear by toilet-training toddlers, by older children experiencing childhood enuresis, and by adults experiencing incontinence. Tape configuration absorbent articles are typically marketed for use with younger babies, and are typically packaged in a folded but an unfastened configuration, such that an article may be withdrawn from the package, opened toward a flat configuration, ready to be pushed rear-waist-edge-first to a location beneath a reclining baby's buttocks/lower torso or to have the baby lowered thereonto in a reclining position, for fitting and fastening. A taped and/or pant-style absorbent article may be useful, for example, as a diaper or training pant for an infant or young child, or as an adult incontinence article for the absorption of body exudates, such as urine or feces.

Figure 9:
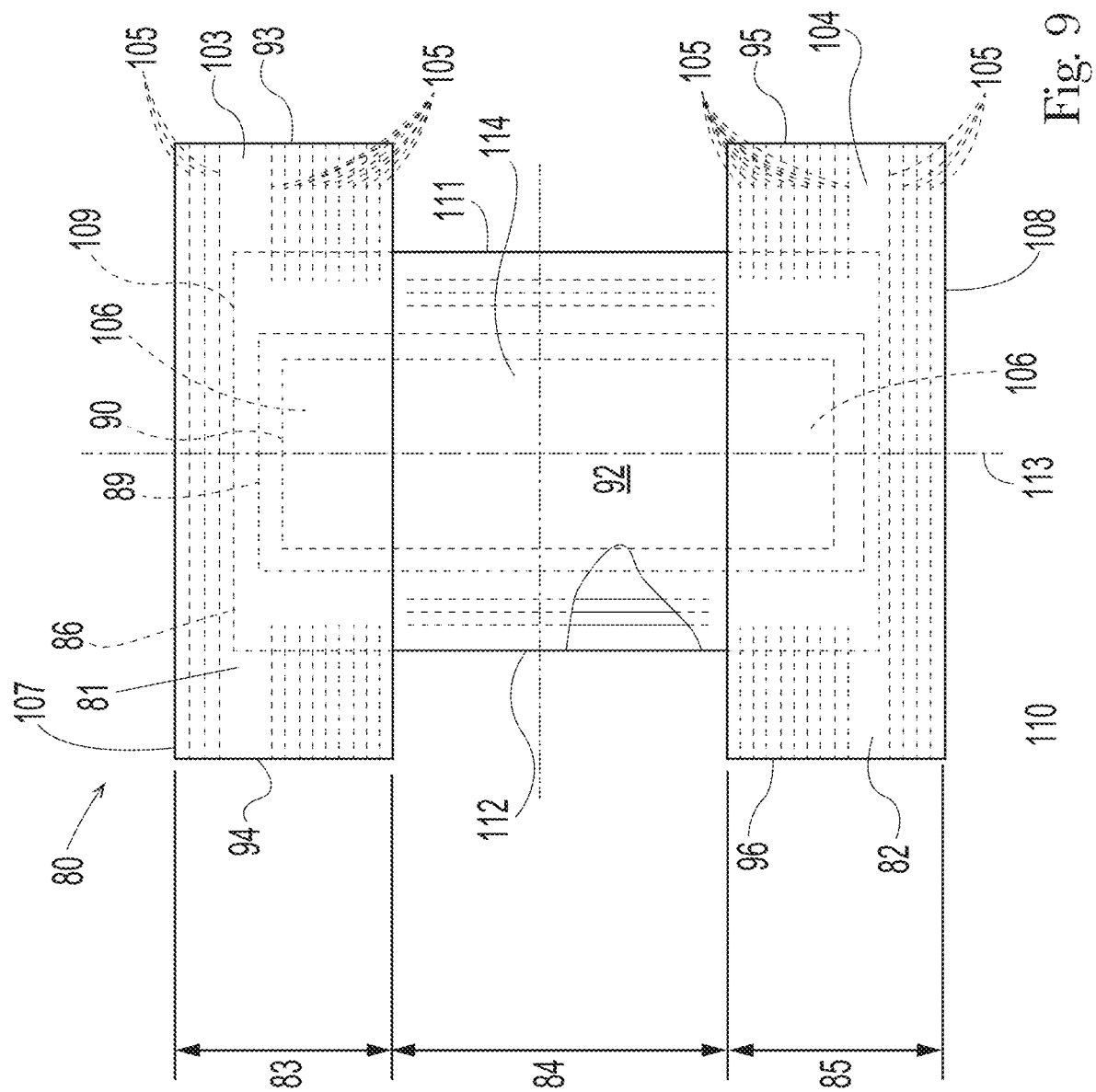
FIG. 9 is a plan view of a pant-style absorbent article.
Figure 10:
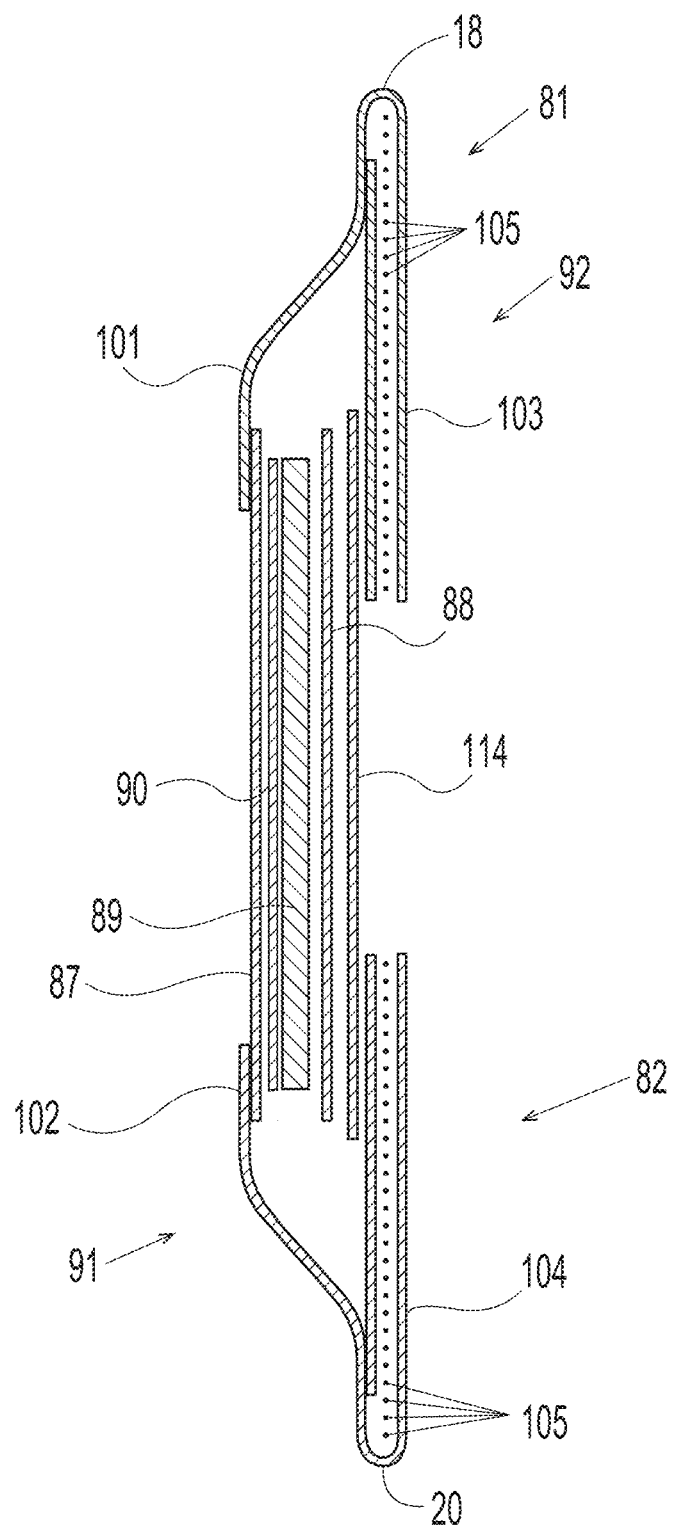
FIG. 10 is an example cross-sectional view of a pant-style absorbent article taken about line 7-7 of FIG. 8.
Figure 11:
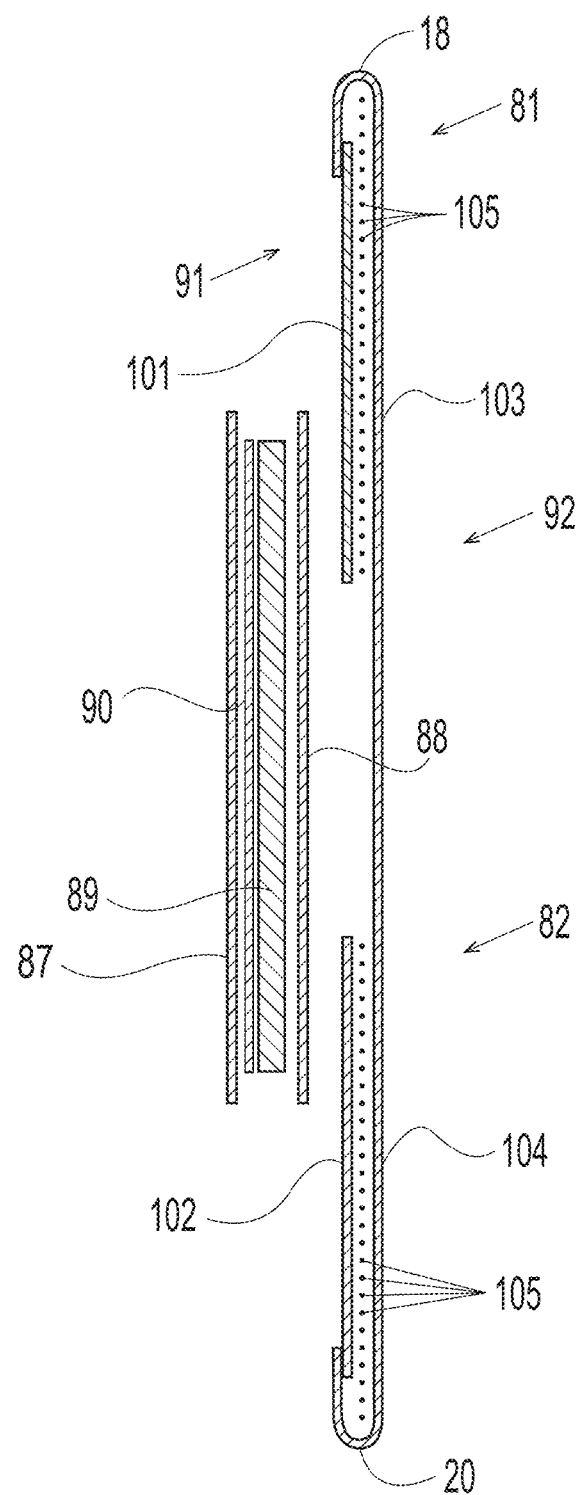
FIG. 11 is an example cross-sectional view of a pant-style absorbent article taken about line 8-8 of FIG. 8.

The absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 8-11, an example absorbent article 80 in the form of a pant is illustrated. FIG. 8 is a front perspective view of the pant-style absorbent article 80. FIG. 9 is a plan view of the pant-style absorbent article 10, laid flat, with the garment-facing surface facing the viewer. Elements of FIG. 8-11 having the same reference number may be the same element. FIG. 10 is an example cross-sectional view of the pant-style absorbent article taken about line 7-7 of FIG. 8. FIG. 11 is an example cross-sectional view of the pant-style absorbent article taken about line 8-8 of FIG. 8. FIGS. 10 and 11 illustrate example forms of front and back belts 81, 82. The absorbent article 80 may have a front waist region 83, a crotch region 84, and a back waist region 85. Each of the regions 83, 84, and 85 may be ⅓ of the length of the absorbent article 80. The absorbent article 80 may have a chassis 86 (sometimes referred to as a central chassis or central panel) comprising a topsheet 87, a backsheet 88, and an absorbent core 89 disposed at least partially intermediate the topsheet 87 and the backsheet 88, and an optional acquisition material 90. The absorbent article 80 may comprise a front belt 81 in the front waist region 82 and a back belt 82 in the back waist region 85. The chassis 86 may be joined to a wearer-facing surface 91 of the front and back belts 81, 82 or to a garment-facing surface 92 of the belts 81, 82. Side edges 93 and 94 of the front belt 81 may be joined to side edges 95 and 96, respectively, of the back belt 82 to form two side seams 97. The side seams 97 may be any suitable seams known to those of skill in the art, such as butt seams or overlap seams, for example. When the side seams 97 are permanently formed or refastenably closed, the absorbent article 80 in the form of a pant has two leg openings 98 and a waist opening circumference 99. The side seams 97 may be permanently joined using adhesives or bonds, for example, or may be refastenably closed using hook and loop fasteners, for example.

Belts

Referring to FIGS. 10 and 11, the front and back belts 81 and 82 may comprise front and back inner belt layers 101 and 102 and front and back outer belt layers 103 and 104 having an elastomeric material (e.g., strands 105 or a film (which may be apertured)) disposed at least partially therebetween. The elastic elements 105 or the film may be relaxed (including being cut) to reduce elastic strain over the absorbent core 89 or, may alternatively, run continuously across the absorbent core 89. The elastics elements 105 may have uniform or variable spacing therebetween in any portion of the belts. The elastic elements 105 may also be pre-strained the same amount or different amounts. The front and/or back belts 81 and 82 may have one or more elastic element free zones 106 where the chassis 86 overlaps the belts 81, 82. In other instances, at least some of the elastic elements 105 may extend continuously across the chassis 86.

The front and back inner belt layers 101, 102 and the front and back outer belt layers 103, 104 may be joined using adhesives, heat bonds, pressure bonds or thermoplastic bonds. Various suitable belt layer configurations can be found in U.S. Pat. Appl. Pub. No. 2013/0211363.

Front and back belt end edges 107 and 108 may extend longitudinally beyond the front and back chassis end edges 109 and 110 (as shown in FIG. 9) or they may be co-terminus. The front and back belt side edges 93, 94, 95, and 96 may extend laterally beyond the chassis side edges 111 and 112. The front and back belts 81 and 82 may be continuous (i.e., having at least one layer that is continuous) from belt side edge to belt side edge (e.g., the transverse distances from 93 to 94 and from 95 to 96). Alternatively, the front and back belts 81 and 82 may be discontinuous from belt side edge to belt side edge (e.g., the transverse distances from 93 to 94 and 95 to 96), such that they are discrete.

As disclosed in U.S. Pat. No. 7,901,393, the longitudinal length (along the central longitudinal axis 113) of the back belt 82 may be greater than the longitudinal length of the front belt 81, and this may be particularly useful for increased buttocks coverage when the back belt 82 has a greater longitudinal length versus the front belt 81 adjacent to or immediately adjacent to the side seams 97.

The front outer belt layer 103 and the back outer belt layer 104 may be separated from each other, such that the layers are discrete or, alternatively, these layers may be continuous, such that a layer runs continuously from the front belt end edge 107 to the back belt end edge 108. This may also be true for the front and back inner belt layers 101 and 102—that is, they may also be longitudinally discrete or continuous. Further, the front and back outer belt layers 103 and 104 may be longitudinally continuous while the front and back inner belt layers 101 and 102 are longitudinally discrete, such that a gap is formed between them—a gap between the front and back inner and outer belt layers 101, 102, 103, and 104 is shown in FIG. 10 and a gap between the front and back inner belt layers 101 and 102 is shown in FIG. 11.

The front and back belts 81 and 82 may include slits, holes, and/or perforations providing increased breathability, softness, and a garment-like texture. Underwear-like appearance can be enhanced by substantially aligning the waist and leg edges at the side seams 97 (see FIG. 8). The dark-tinted nonwoven webs of the present disclosure may form any nonwoven portion or portions of the front and back belts.

Alternatively, instead of attaching belts 81 and 82 to the chassis 86 to form a pant, discrete side panels may be attached to side edges of the chassis 111 and 112. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744. The dark-tinted nonwoven webs of the present disclosure may form portions of, or all of, discrete side panels.

The outer cover material (sometimes referred to as a backsheet nonwoven) 114 may comprise one or more nonwoven materials joined to the backsheet 88 and that covers the backsheet 88. The outer cover material 114 forms at least a portion of the garment-facing surface 92 of the absorbent article 80 and effectively "covers" the backsheet 88 so that film is not present on the garment-facing surface 92. The outer cover material 114 may comprise a bond pattern, apertures, and/or three-dimensional features. The dark-tinted nonwoven webs of the present disclosure may form portions of, or all of, the outer cover.

EXAMPLES

Comparative Example 1

The nonwoven web described herein as Comparative Example 1 is a nonwoven web comprising spunbond and meltblown filaments in an SMMMMS configuration. The basis weight of the spunbond layers is between about 12 and 13 gsm, and the basis weight of the meltblown layers is between about 2 and 3 gsm. Both the spunbond filaments and the meltblown filaments comprise a high purity black pigment. The total basis weight of the nonwoven web is about 15 gsm.

Comparative Example 2

The nonwoven web described herein as Comparative Example 2 is a nonwoven web comprising spunbond and meltblown filaments in a SMMMMS configuration. The overall basis weight of the spunbond layers is between about 13 and 14 gsm, and the overall basis weight of the meltblown layers is between about 1 and 1.5 gsm. Only the spunbond filaments comprise a high purity black pigment at a level of 1.5 times that of Comparative Example 1. The total basis weight of the nonwoven web is about 15 gsm.

Example 1

The nonwoven web described herein as Example 1 is a nonwoven web comprising spunbond and meltblown filaments in an SMMMMS configuration. The basis weight of the spunbond layers is between about 12 and 13 gsm, and the basis weight of the meltblown layers is about between about 2 and 3 gsm. Both the spunbond filaments and the meltblown filaments comprise a high purity black pigment. The spunbond filaments comprise black pigment at the same level as that of Comparative Example 1. The meltblown filaments comprise black pigment at a level of 1.5 times that of Comparative Example 1. The total basis weight of the nonwoven web is about 15 gsm.

Example 2

The dark-tinted nonwoven web described herein as Example 2 is a nonwoven web comprising spunbond and meltblown filaments in an SMMMMS configuration. The basis weight of the spunbond layers is between about 13 and 14 gsm, and the basis weight of the meltblown layers is about between about 1 and 1.5 gsm. Both the spunbond filaments and the meltblown filaments comprise a high purity black pigment. The spunbond filaments comprise black pigment at the same level as that of Comparative Example 1. The meltblown filaments comprise a high purity black pigment at a level of 2.25 times that of Comparative Example 1. The total basis weight of the nonwoven web is about 15 gsm.

Example 3

The dark-tinted nonwoven web described herein as Example 3 is a nonwoven web comprising spunbond and meltblown filaments in an SMMMMS configuration. The basis weight of the spunbond layers is between about 13 and 14 gsm, and the basis weight of the meltblown layers is between about 1 and 1.5 gsm. Both the spunbond filaments and the meltblown filaments comprise a high purity black pigment. The spunbond filaments comprise a high purity black pigment at a level of 1.5 that of Comparative Example 1. The meltblown filaments comprise a high purity black pigment at a level of 2.25 times that of Comparative Example 1. The total basis weight of the nonwoven web is about 15 gsm.

Example 4

The dark-tinted nonwoven web described herein as Example 4 is a nonwoven web comprising spunbond and meltblown filaments in an SMMS configuration. The basis weight of the spunbond layers is between about 13.5 and 14.5 gsm, and the basis weight of the meltblown layers is between about 0.5 and 1 gsm. Both the spunbond filaments and the meltblown filaments comprise a high purity black pigment. The spunbond filaments comprise a high purity black pigment at a level of 1.5 that of Comparative Example 1. The meltblown filaments comprise a high purity black pigment at a level of 2.25 times that of Comparative Example 1. The total basis weight of the nonwoven web is about 15 gsm.

TABLE 1

CIE L*a*b* Color Measurements

| Sample Number | Color | | | Pigment Levels | |
| --- | --- | --- | --- | --- | --- |
| | L* (±S.D.) | a* (±S.D.) | b* (±S.D.) | Spunbond | Meltblown |
| Comparative Example 1 | 30.53 ± 0.93 | 0.46 ± 0.04 | 1.70 ± 0.08 | 1x | 1x |
| Comparative Example 2 | 32.75 ± 2.1 | 0.50 ± 0.03 | 1.56 ± 0.07 | 1.5x | 0 |
| Example 1 | 26.12 ± 0.59 | 0.78 ± 0.01 | 2.32 ± 0.04 | 1x | 1.5x |
| Example 2 | 25.18 ± 0.58 | 0.48 ± 0.03 | 2.45 ± 0.06 | 1x | 2.25x |
| Example 3 | 23.61 ± 0.50 | 0.66 ± 0.01 | 2.09 ± 0.06 | 1.5x | 2.25x |
| Example 4 | 22.69 ± 0.73 | 0.56 ± 0.02 | 1.77 ± 0.07 | 1.5x | 2.25x |

Comparative Examples 1-2 and Examples 1-4 were analyzed for color characteristics according to the CIE L*a*b* Test described herein. Eight layers of the nonwoven are stacked to form a composite sample for analysis. The L* variable of the CIE L*a*b* test analyzes for darkness of a product, with a value of 0 being black, and a value of 100 being white.

Comparative Examples 1 and 2 have L* values greater than 30, while Examples 1-4 all have L* values of between about 0 and about 26. Comparative Example 1 has a relatively low spunbond filament basis weight. The data suggest that increasing the basis weight of the spunbond filament portion of the nonwoven web may produce a darker web where the pigment loading stays the same or increases (Examples 3 and 4). Although Comparative Example 2 has an increased spunbond basis weight, the meltblown filaments did not comprise a pigment, thus decreasing the overall L* value of the sample. Removal of pigment from the meltblown filament negatively impacted the dark color of Comparative Example 2, even while simultaneously increasing the pigment concentration in the spunbond filaments. This suggests that the light color of the meltblown layer may be seen through the pigmented spunbond layer, causing an overall lighter appearance.

Increasing the ratio of spunbond filaments to meltblown filaments appears to produce a darker color (Examples 2-4), either while maintaining pigment concentrations or increasing them. Without wishing to be bound by theory, it is believed that poor dispersion of pigment within the polymer matrix of the meltblown filaments may detrimentally impact the L* value of the material web. Sufficient spunbond filaments may be needed to cover the meltblown filaments that are lighter in color due to poor dispersion of pigment.

Comparative Example 3

The nonwoven web described herein as Comparative Example 3 is a nonwoven web, each layer comprising spunbond filaments in an SSS configuration. The spunbond filaments comprise a high purity black pigment, and the total basis weight of the nonwoven web is 22 gsm.

Example 5

The nonwoven web described herein as Example 5 is a nonwoven web comprising spunbond and meltblown filaments in an SSMMMS configuration. Both the spunbond filaments and the meltblown filaments comprise a high purity black pigment. The total basis weight of the nonwoven web is about 15 gsm.

TABLE 2

Hydrohead Values

| Sample Number | Composition (basis wt.) | Mean Hydrohead Value (mbar) | Std. Dev. |
| --- | --- | --- | --- |
| Comparative Example 3 | SSS (22 gsm) | 14.20 | 2.00 |
| Example 5 | SSMMMS (15 gsm) | 21.6 | 2.27 |

Comparative Example 3 and Example 5 were tested for fluid barrier properties using the Hydrostatic Head Test described herein. Following the Hydrostatic Head Test, ten measurements were made on each sample. Comparative Example 3 exhibited a hydrohead value of 14.20 mbar, while Example 5 exhibited a hydrohead value of 29.10, demonstrating that Example 5 has more robust fluid barrier properties as compared to Comparative Example 2.

As discussed above and without wishing to be bound by theory, it is believed that smaller diameter meltblown filaments provide a barrier against the flow of, or at least to slow the flow of fluid through the nonwoven web. Example 5, comprising small diameter meltblown filaments, exhibits a greater barrier against fluid transmission through the nonwoven web as shown by the greater fluid pressure required to transfer the sample fluid through the nonwoven web sample.

Test Procedures
Filament Size Test and Filament Ratio Test

A Scanning Electron Microscope (SEM) is used to obtain images of both the first side (e.g. SL side) and second side (e.g. L side) of a nonwoven test sample. From these images, the size (i.e. diameter) and quantity of the filaments on each side of the test sample is determined using image analysis. All testing is performed in a room maintained at a temperature of 23° C.±2.0° C. and a relative humidity of 50%±2% and samples are conditioned under the same environmental conditions for at least 2 hours prior to testing.

Obtain a test sample by removing it from an absorbent article, if necessary. When excising the sample from an absorbent article, use care to not impart any contamination or distortion to the sample layer during the process. The test sample is obtained from an area free of folds or wrinkles. A total of 6 replicate test samples are obtained. The test region on each test sample is marked in such a way that will allow for the same area to be analyzed on each side. One suitable way to mark the sidedness of the test region is to use an asymmetrical notch.

Secondary Electron (SE) images are obtained using an SEM such as the FEI Quanta 450 (available from FEI Company, Hillsboro, OR), or equivalent. The instrument is calibrated according to the manufacturer's instructions prior to use to ensure an accurate distance scale. The test region on the first side of the test sample is viewed at a low magnification (e.g. 200×; horizontal field width about 1 mm) such that a representative number of the larger filaments are clearly visualized for counting purposes, and an image is acquired. Now the first side of the test sample is viewed at a high magnification (e.g. 1000×; horizontal field width about 200 microns) such that the size (diameter) of the filaments can accurately be measured, and an image is acquired. At the same test region, images of the second side of the test sample are acquired using the same low and high magnification used for the first side.

The high magnification image of the first side of the test sample is opened on a computer running image analysis software, such as Image Pro Plus (available from Media Cybernetics, Rockville, MD), or equivalent. The calibrated distance scale is used to measure the Filament Size (diameter) of both the larger diameter filaments (e.g. spunbond filaments; "first plurality") and the smaller diameter filaments (e.g. meltblown filaments; "second plurality"), and these values are recorded as Large Filament Size and Small Filament Size, respectively, to the nearest 0.01 micron. The diameter of each filament is measured at a location that is perpendicular to the fiber length at each specific measurement location. Examples of high magnification images with labeled filament diameters can be seen in FIGS. 1 and 7. In like fashion, the Large Filament Size and Small Filament Size (diameters) are measured on the high magnification image of the second side of the test sample, and each recorded to the nearest 0.01 micron. Now open the low magnification image of the first side of the test sample. All of the larger diameter filaments (e.g. spunbond filaments) within the image are manually counted and the number recorded as Filaments$_{Side\ 1}$. To prevent counting a filament more than once, each counted filament is "marked" on the image. Examples of low magnification images with marked filaments can be seen in FIGS. 2, 8 and 9. In like fashion, the number of larger diameter filaments are counted on the low magnification image of the second side of the test sample at the same test region, and the number recorded as Filaments$_{Side\ 2}$. Calculate the Filament Ratio by dividing Filaments$_{Side\ 2}$ by Filaments$_{Side\ 1}$ and record to the nearest 1 unit.

In like fashion, repeat all measurements for a total of 6 replicate test samples. Calculate the arithmetic mean for Filament Ratio obtained for all 6 replicates and report to the nearest 1 unit. Calculate the arithmetic mean for Large Filament Size and Small Filament Size for all 6 replicates and report each to the nearest 0.01 micron.

CIE L*a*b* Test

Color analyses are made using a 0°/45° spectrophotometer with adjustable apertures capable of making standard CIE L*a*b* measurements in accordance with ASTM E1349. An example of a suitable spectrophotometer is the Labscan XE (available from Hunter Associates Laboratory, Inc., Reston, VA, or equivalent). Dark tinted nonwoven webs are tested as a sample of eight layers of nonwoven web from the same material. All testing is performed in a room maintained at a temperature of 23° C.±2.0° C. and a relative humidity of 50%±2% and samples are conditioned under the same environmental conditions for at least 2 hours prior to testing.

Obtain a sample by removing it from an absorbent article, if necessary. When excising the sample from an absorbent article, use care to not impart any contamination or distortion to the sample layer during the process. The sample is obtained from an area free of folds or wrinkles, and it must be larger than the aperture used on the spectrophotometer. Obtain a sufficient quantity of the sample such that, ideally, ten measurements can be made on non-overlapping areas of an individual test material. If the material to be tested has a small area, alternatively ten separate samples may be used. The number of layers to be used for the measurement must be taken into account when acquiring the sample.

To measure Color, calibrate and standardize the instrument per the vendor instructions using the standard white, green and black tiles provided by the vendor. Set the spectrophotometer to use the CIE L*a*b* color space with a D65 standard illumination, a 10° observer, a 0.25 inch area view, a 0.40 inch aperture, and the UV filter set to nominal. Place the sample centered over the aperture with the side to be measured facing the aperture. Place the standard white tile behind the sample, take a reading and record L*a*b* values to the nearest 0.01 units, noting how many layers were tested.

In like fashion, repeat for a total of ten measurements on non-overlapping areas of the sample, or alternatively on ten separate samples of the same test material. Calculate the arithmetic mean for L*, a* and b* values obtained from all ten measurements and report each to the nearest 0.01 unit. The number of layers tested must also be reported with each value.

Hydrostatic Head Test

The Hydrostatic Head Test measures the fluid barrier functionality of a nonwoven test sample. A hydrostatic head tester is used to make the measurements in accordance with WSP 80.6. A suitable instrument is the TexText Hydrostatic Head Tester FX3000 (available from Advanced Testing Instruments, Corp., Spartanburg, SC), or equivalent. In order to accommodate very small test samples (e.g. leg cuffs), the hydrostatic head tester is equipped with a very small test head (1 to 2 cm$^2$; also available from Advanced Testing Instruments as a custom order). During the test, the test sample is subjected to increasing water pressure at a rate of 20 mbar/min until water penetrates through the sample. All testing is performed in a room maintained at a temperature of 23° C.±2.0° C. and a relative humidity of 50%±2% and samples are conditioned under the same environmental conditions for at least 2 hours prior to testing.

Obtain a test sample by removing it from an absorbent article, if necessary, and note which side of the sample faces (or is intended to face) the outermost side (wearer-side) of the article. The test sample should comprise one layer of nonwoven web. When excising the sample from an absorbent article, use care to not impart any contamination or distortion to the sample layer(s) during the process. Ideally, the test sample is obtained from an area free of folds or wrinkles and areas that include seams or bond areas are avoided. The test sample must be larger than the opening of the test head used on the hydrostatic head tester. Obtain a sufficient quantity of the test material such that five replicate test samples can be measured.

To test the sample, clamp it onto the hydrostatic head tester with the wearer-side facing away from the water. Start the test such that the water pressure is increased at a rate of 20 mbar/min. Record the pressure when the first droplet of water penetrates through the test sample. The test result is recorded as the pressure when the first droplet of water penetrates through the test sample, and the test is stopped. Details regarding the interpretation of the results can be found in WSP 80.6.

In like fashion, repeat the test for a total of ten replicate test samples. Calculate the arithmetic mean for the Hydrohead Values recorded at the first drop from all ten measurements and report to the nearest 0.01 mbar.

Combinations

A. An absorbent article comprising:
a topsheet;
a backsheet;
an absorbent core disposed between the topsheet and the backsheet; and
a pair of barrier cuffs extending longitudinally along sides of the absorbent article comprising a nonwoven web comprising:
a first plurality of filaments having a diameter between about 8 μm and about 50 μm according to the Filament Size Test, wherein the first plurality of filaments comprise a pigment; and
a second plurality of filaments having a diameter between about 0.3 μm and about 5 μm according to the Filament Size Test;
wherein the nonwoven web comprises a first side and an opposing second side, wherein the first plurality of filaments forms a portion of the first side and wherein the first plurality of filaments forms a portion of the second side; and
wherein the nonwoven web has an L* value of between about 0 and about 26 as measured from either the first side or the second side, according to the CIE L*a*b* Test.

B. The absorbent article of Paragraph A, wherein a First Filament Ratio of the number of filaments of the first plurality of filaments as measured from the first side to the number of filaments of the first plurality of filaments as measured from the second side is between about 1.5 to 1 and about 4 to 1, according to the Filament Ratio Test.

C. The absorbent article of Paragraph B, wherein the First Filament Ratio is between about 2 and about 3.5.

D. The absorbent article of Paragraph B, wherein the First Filament Ratio is between about 2.25 and about 3.

E. The absorbent article of any one of Paragraphs A-D, wherein the pigment is a black pigment.

F. The absorbent article of Paragraph E, wherein the black pigment comprises a high purity pigment.

G. The absorbent article of any one of Paragraphs E-F, wherein the black pigment is carbon black.

H. The absorbent article of any one of Paragraphs A-G, wherein the nonwoven web has an L* value of between about 0 and about 26, as measured from the first side, according to the CIE L*a*b* Test.

I. The absorbent article of any one of Paragraphs A-H, wherein the nonwoven web has a basis weight of between about 10 gsm to about 50 gsm.

J. The absorbent article of any one of Paragraphs A-H, wherein the nonwoven web has a basis weight of between about 11 gsm to about 30 gsm.

K. The absorbent article of any one of Paragraphs A-H, wherein the nonwoven web has a basis weight of between about 13 gsm to about 22 gsm.

L. The absorbent article of any one of Paragraphs A-K, wherein the nonwoven web has Hydrohead Value of between about 15 mbar and about 50 mbar, according to the Hydrostatic Head Test.

M. An absorbent article comprising:
a topsheet;
a backsheet;
an absorbent core disposed between the topsheet and the backsheet; and
a pair of barrier cuffs extending longitudinally along sides of the absorbent article comprising a nonwoven web comprising:
a first plurality of filaments having a diameter between about 8 μm and about 50 μm according to the Filament Size Test, wherein the first plurality of filaments comprise a first pigment; and
a second plurality of filaments having a diameter between about 0.3 μm and about 5 μm according to the Filament Size Test, wherein the second plurality of filaments comprise a second pigment;
wherein the nonwoven web comprises a first side and an opposing second side, wherein the first plurality of filaments forms a portion of the first side and wherein the first plurality of filaments forms a portion of the second side; and
wherein the nonwoven web has an L* value of between about 0 and about 26 as measured from either the first side or the second side, according to the CIE L*a*b* Test.

N. The absorbent article of Paragraph M, wherein a First Filament Ratio of the number of filaments of the first plurality of filaments as measured from the first side to the number of filaments of the first plurality of filaments as measured from the second side is between about 1.25 to 1 and about 3.5 to 1, according to the Filament Ratio Test.

O. The absorbent article of Paragraph M, wherein a First Filament Ratio of the number of filaments of the first plurality of filaments as measured from the first side to the number of filaments of the first plurality of filaments as measured from the second side is between about 1.5 to 1 and about 3 to 1, according to the Filament Ratio Test.

P. The absorbent article of Paragraph M, wherein a First Filament Ratio of the number of filaments of the first plurality of filaments as measured from the first side to the number of filaments of the first plurality of filaments as measured from the second side is between about 1.75 to 1 and about 2.75 to 1, according to the Filament Ratio Test.

Q. The absorbent article of any one of Paragraphs M-P, wherein the first and second pigments comprise black pigments.

R. The absorbent article of Paragraph Q, wherein the black pigments comprise high purity pigments.

S. The absorbent article of any one of Paragraphs Q-R, wherein the black pigments are carbon black.

T. The absorbent article of any one of Paragraphs M-S, wherein the nonwoven web comprises an L* value of between about 0 and about 26, as measured from the first side according to the CIE L*a*b* Test.

U. The absorbent article of any one of Paragraphs M-T, wherein the nonwoven web has a basis weight of between about 10 gsm to about 50 gsm.

V The absorbent article of any one of Paragraphs M-T, wherein the nonwoven web has a basis weight of between about 11 gsm to about 30 gsm.

W. The absorbent article of any one of Paragraphs M-T, wherein the nonwoven web has a basis weight of between about 13 gsm to about 22 gsm.

X. The absorbent article of any one of Paragraphs M-W, wherein the nonwoven web has a Hydrohead value of between about 15 mbar and about 50 mbar, according to the Hydrostatic Head Test.

Y An absorbent article comprising:
a topsheet;
a backsheet;
an absorbent core disposed between the topsheet and the backsheet; and
a pair of barrier cuffs extending longitudinally along sides of the absorbent article;
wherein a component of the absorbent article comprises a nonwoven web comprising:
a first plurality of filaments having a diameter between about 8 µm and about 50 µm according to the Filament Size Test, wherein the first plurality of filaments comprise a pigment;
a second plurality of filaments having a diameter between about 0.3 µm and about 5 µm according to the Filament Size Test;
wherein the nonwoven web comprises a first side and an opposing second side, wherein the first plurality of filaments forms a portion of the first side and wherein the first plurality of filaments forms a portion of the second side; and
wherein the nonwoven web has an L* value of between about 0 and about 26 as measured from either the first side or the second side, according to the CIE L*a*b* Test.

Z. The absorbent article of Paragraph Y, wherein a First Filament Ratio of the number of filaments of the first plurality of filaments as measured from the first side to the number of filaments of the first plurality of filaments as measured from the second side is between about 1.5 to 1 and about 4 to 1, according to the Filament Ratio Test.

AA. The absorbent article of Paragraph Y, wherein a First Filament Ratio of the number of filaments of the first plurality of filaments as measured from the first side to the number of filaments of the first plurality of filaments as measured from the second side is between about 2 to 1 and about 3.5 to 1, according to the Filament Ratio Test.

BB. The absorbent article of Paragraph Y, wherein a First Filament Ratio of the number of filaments of the first plurality of filaments as measured from the first side to the number of filaments of the first plurality of filaments as measured from the second side is between about 2.25 to 1 and about 3 to 1, according to the Filament Ratio Test.

CC. The absorbent article of any one of Paragraphs Y-BB, wherein the pigment is a black pigment.

DD. The absorbent article of Paragraph CC, wherein the black pigment comprises a high purity pigment.

EE. The absorbent article of any one of Paragraphs CC-DD, wherein the black pigment is carbon black.

FF. The absorbent article of any one of Paragraphs Y-EE, wherein the nonwoven web has an L* value of between about 0 and about 26, as measured from the first side, according to the CIE L*a*b* Test.

GG. The absorbent article of any one of Paragraphs Y-FF, wherein the nonwoven web has a basis weight of between about 10 gsm to about 50 gsm.

HH. The absorbent article of any one of Paragraphs Y-FF, wherein the nonwoven web has a basis weight of between about 11 gsm to about 30 gsm.

II. The absorbent article of any one of Paragraphs Y-FF, wherein the nonwoven web has a basis weight of between about 13 gsm to about 22 gsm.

JJ. The absorbent article of any one of Paragraphs Y-II, wherein the nonwoven web has Hydrohead Value of between about 15 mbar and about 50 mbar, according to the Hydrostatic Head Test.

KK. An absorbent article comprising:
a topsheet;
a backsheet;
an absorbent core disposed between the topsheet and the backsheet; and
a pair of barrier cuffs extending longitudinally along sides of the absorbent article;
wherein a component of the absorbent article comprises a nonwoven web comprising:
a first plurality of filaments having a diameter between about 8 µm and about 50 µm according to the Filament Size Test, wherein the first plurality of filaments comprise a first pigment;
a second plurality of filaments having a diameter between about 0.3 µm and about 5 µm according to the Filament Size Test, wherein the second plurality of filaments comprise a second pigment;
wherein the nonwoven web comprises a first side and an opposing second side, wherein the first plurality of filaments forms a portion of the first side and wherein the first plurality of filaments forms a portion of the second side; and
wherein the nonwoven web has an L* value of between about 0 and about 26 as measured from either the first side or the second side, according to the CIE L*a*b* Test.

LL. The absorbent article of Paragraph KK, wherein a First Filament Ratio of the number of filaments of the first plurality of filaments as measured from the first side to the number of filaments of the first plurality of filaments as measured from the second side is between about 1.25 to 1 and about 3.5 to 1, according to the Filament Ratio Test.

MM. The absorbent article of Paragraph KK, wherein a First Filament Ratio of the number of filaments of the first plurality of filaments as measured from the first side to the number of filaments of the first plurality of filaments as measured from the second side is between about 1.5 to 1 and about 3 to 1, according to the Filament Ratio Test.

NN. The absorbent article of Paragraph KK, wherein a First Filament Ratio of the number of filaments of the first plurality of filaments as measured from the first side to the number of filaments of the first plurality of filaments as measured from the second side is between about 1.75 to 1 and about 2.75 to 1, according to the Filament Ratio Test.

OO. The absorbent article of any one of Paragraphs KK-NN, wherein the pigment is a black pigment.

PP. The absorbent article of Paragraph OO, wherein the black pigment comprises a high purity pigment.

QQ. The absorbent article of any one of Paragraphs OO-PP, wherein the black pigment is carbon black.

RR. The absorbent article of any one of Paragraphs KK-QQ, wherein the nonwoven web has an L* value of between about 0 and about 26, as measured from the first side, according to the CIE L*a*b* Test.

SS. The absorbent article of any one of Paragraphs KK-RR, wherein the nonwoven web has a basis weight of between about 10 gsm to about 50 gsm.

TT. The absorbent article of any one of Paragraphs KK-RR, wherein the nonwoven web has a basis weight of between about 11 gsm to about 30 gsm.

UU. The absorbent article of any one of Paragraphs KK-RR, wherein the nonwoven web has a basis weight of between about 13 gsm to about 22 gsm.

VV. The absorbent article of any one of Paragraphs KK-UU, wherein the nonwoven web has Hydrohead Value of between about 15 mbar and about 50 mbar, according to the Hydrostatic Head Test.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a topsheet;
a backsheet;
an absorbent core disposed between the topsheet and the backsheet; and
a pair of barrier cuffs extending longitudinally along sides of the absorbent article, each of the pair of barrier cuffs comprising a nonwoven web comprising:
a first plurality of filaments having a diameter between about 8 μm and about 50 μm according to the Filament Size Test, wherein the first plurality of filaments comprise a first pigment; and
a second plurality of filaments having a diameter between about 0.3 μm and about 5 μm according to the Filament Size Test, wherein the second plurality of filaments comprise a second pigment;
wherein the nonwoven web comprises a first side and an opposing second side, wherein the first plurality of filaments forms a portion of the first side and wherein the first plurality of filaments forms a portion of the second side; and
wherein the nonwoven web has an L* value of between about 0 and about 26 as measured from either the first side or the second side, according to the CIE L*a*b* Test;
wherein the first plurality of filaments has a basis weight of between about 12 to about 25 gsm;
wherein the second plurality of filaments has a basis weight of between about 0.5 to about 3 gsm;
wherein at least one of the first plurality of filaments and the second plurality of filaments have a ratio of colorant particle diameter to filament diameter of less than 0.07.

2. The absorbent article of claim 1, wherein a First Filament Ratio of the number of filaments of the first plurality of filaments as measured from the first side to the number of filaments of the first plurality of filaments as measured from the second side is between about 1.25 to 1 and about 3.5 to 1, according to the Filament Ratio Test.

3. The absorbent article of claim 1, wherein the first and/or second pigments comprise black pigment.

4. The absorbent article of claim 3, wherein the black pigment comprises a high purity pigment.

5. The absorbent article of claim 3, wherein the black pigment is carbon black.

6. The absorbent article of claim 2, wherein the nonwoven web comprises an L* value of between about 0 and about 26, as measured from the first side according to the CIE L*a*b* Test.

7. The absorbent article of claim 1, wherein the nonwoven web has a basis weight of between about 10 gsm to about 50 gsm.

8. The absorbent article of claim 1, wherein the nonwoven web has a Hydrohead value of between about 15 mbar and about 50 mbar, according to the Hydrostatic Head Test.

9. An absorbent article comprising:
a topsheet;
a backsheet;
an absorbent core disposed between the topsheet and the backsheet; and
a pair of barrier cuffs extending longitudinally along sides of the absorbent article;
wherein a component of the absorbent article comprises a nonwoven web comprising:
a first plurality of filaments having a diameter between about 8 μm and about 50 μm according to the Filament Size Test, wherein the first plurality of filaments comprise a first pigment;
a second plurality of filaments having a diameter between about 0.3 μm and about 5 μm according to the Filament Size Test;
wherein the nonwoven web comprises a first side and an opposing second side, wherein the first plurality of filaments forms a portion of the first side and wherein the first plurality of filaments forms a portion of the second side; and
wherein the nonwoven web has an L* value of between about 0 and about 26 as measured from either the first side or the second side, according to the CIE L*a*b* Test;
wherein the first plurality of filaments has a basis weight of between about 12 to about 25 gsm;
wherein the second plurality of filaments has a basis weight of between about 0.5 to about 3 gsm;
wherein at least one of the first plurality of filaments and the second plurality of filaments have a ratio of colorant particle diameter to filament diameter of less than 0.07.

10. The absorbent article of claim 9, wherein a First Filament Ratio of the number of filaments of the first plurality of filaments as measured from the first side to the number of filaments of the first plurality of filaments as measured from the second side is between about 1.5 to 1 and about 4 to 1, according to the Filament Ratio Test.

11. The absorbent article of claim 9, wherein the second plurality of filaments comprise a second pigment, and wherein a First Filament Ratio of the number of filaments of the first plurality of filaments as measured from the first side to the number of filaments of the first plurality of filaments as measured from the second side is between about 1.25 to 1 and about 3.5 to 1, according to the Filament Ratio Test.

12. The absorbent article of claim 11, wherein the first and/or second pigment is a black pigment.

13. The absorbent article of claim 12, wherein the black pigment comprises a high purity pigment.

14. The absorbent article of claim 12, wherein the black pigment is carbon black.

15. The absorbent article of claim 10, wherein the nonwoven web has an L* value of between about 0 and about 26, as measured from the first side, according to the CIE L*a*b* Test.

16. The absorbent article of claim 9, wherein the nonwoven web has Hydrohead Value of between about 15 mbar and about 50 mbar, according to the Hydrostatic Head Test.

* * * * *